(12) United States Patent
Yarmush et al.

(10) Patent No.: US 9,709,554 B2
(45) Date of Patent: Jul. 18, 2017

(54) IN VITRO MODEL OF MACROSTEATOTIC (FATTY) LIVER

(71) Applicant: Rutgers, The State University of New Jersey, New Brunswick, NJ (US)

(72) Inventors: Martin L. Yarmush, Newton, MA (US); Nir I. Nativ, West Orange, NJ (US); Francois Berthiaume, Metuchen, NJ (US); Gabriel A. Yarmush, Linden, NJ (US); Tim Maguire, Piscataway, NJ (US); Rene S. Schloss, East Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 116 days.

(21) Appl. No.: 14/169,605

(22) Filed: Jan. 31, 2014

(65) Prior Publication Data

US 2014/0212918 A1    Jul. 31, 2014

Related U.S. Application Data

(60) Provisional application No. 61/759,113, filed on Jan. 31, 2013.

(51) Int. Cl.
*G01N 33/50* (2006.01)
*C12N 5/071* (2010.01)

(52) U.S. Cl.
CPC ......... *G01N 33/5067* (2013.01); *C12N 5/067* (2013.01); *C12N 2533/54* (2013.01)

(58) Field of Classification Search
CPC . G01N 33/5067; C12N 5/067; C12N 2533/54
USPC ....................................................... 435/370
See application file for complete search history.

(56) References Cited

U.S. PATENT DOCUMENTS

| | | | |
|---|---|---|---|
| 5,223,409 A | 6/1993 | Ladner et al. | |
| 2006/0084096 A1* | 4/2006 | Boess | C12Q 1/6876 435/6.13 |
| 2009/0191159 A1 | 7/2009 | Sakurada et al. | |
| 2011/0004260 A1 | 1/2011 | Sherman et al. | |
| 2011/0070647 A1 | 3/2011 | Dezawa et al. | |
| 2012/0244129 A1 | 9/2012 | Dezawa et al. | |

FOREIGN PATENT DOCUMENTS

| | | |
|---|---|---|
| WO | 2011102532 | 8/2011 |
| WO | 2012058868 | 5/2012 |

OTHER PUBLICATIONS

Berthiaume et al. (2009). Steatosis Reversibly Increases Hepatocyte Sensitivity to Hypoxia-Reoxygenation Injury. Journal of Surgical Research, v152, p. 54-60.*
Berthiaume et al., "Steatosis Reversibly Increases Hepatocyte Sensitivity to Hypoxia-Reoxygenation Injury," Journal of Surgical Research., 2009, vol. 152, No. 1, pp. 54-60.

(Continued)

*Primary Examiner* — Scott Long
*Assistant Examiner* — Sean C Barron
(74) *Attorney, Agent, or Firm* — Fox Rothschild LLP

(57) ABSTRACT

The present invention relates to a system and methods for identifying a compound for de-fatting and functional recovery of macrosteatotic hepatocytes.

10 Claims, 18 Drawing Sheets

(56) References Cited

OTHER PUBLICATIONS

Carrell et al., "A Novel Procedure for the Synthesis of Libraries Containing Small Organic Molecules," Angew Chem Int Ed Engl, 1994, vol. 33, pp. 2059-2061 (Abstract).
Carrell et al., "A Solution-Phase Screening Procedure for the Isolation of Active Compounds from a Library of Molecules," Angew Chem Int Ed Engl, 1994, vol. 33, pp. 2061-2064 (Abstract).
Cho et al., "An Unnatural Biopolymer," Sep. 3, 1993, Science, vol. 261, No. 5126, pp. 1303-1305 (Abstract).
Cull et al., "Screening for Receptor Ligands Using Large Libraries of Peptides Linked to the C Terminus of the Lac Repressor," Proc Natl Acas Sci USA, Mar. 1992, vol. 89, pp. 1865-1869.
Cwirla et al., "Peptides on Phage: A Vast Library of Peptides for Identifying Ligands," Proc Natl Acad Sci USA, Aug. 1990, vol. 87, pp. 6378-6382.
de Graaf et al., "Grade of Deceased Donor Liver Macrovesicular Steatosis Impacts Graft and Recipient Outcoumes More Than the Donor Risk Index," J Gastroenterol Hepatol., Mar. 2012, vol. 27, No. 3, pp. 540-546 (Abstract).
Devlin, et al., "Random Peptide Libraries: A Source of Specific Protein Binding Molecules," Science, Jul. 1990, vol. 249(4967), pp. 404-406 (Abstract).
DeWitt et al., "Diversomers': An Approach to Nonpeptide, nonoligomeric Chemical Divesity," Proc Natl Acad Sci USA, Aug. 1993, vol. 90, pp. 6909-6913.
Erb et al., "Recursive Deconvolution of Combinatorial Chemical Libraries," Proc Natl Acad Sci USA, Nov. 1994, vol. 91, pp. 11422-11426.
Felici et al., "Selection of Anitbody Ligands From a LArge Library of Oligopeptides Expressed on a Multivalent Exposition Vector," J. Mol. Biol., Nov. 1991, vol. 222, No. 2, pp. 301-310 (Abstract).
Fodor, et al., "Multiplexed Biochemical Assays with Biological Chips," Nature, Aug. 1993, vol. 364(6437), pp. 555-556 (Abstract).
Gallop et al., "Applications of Cominatorial Technologies to Drug Discovery. 1. Background and Peptide Combinatorial Libraries," J. Med. Chem., Apr. 1994, vol. 37, No. 9, pp. 1233-1251 (Abstract).
Guarrera et al., "Hypothermic Machine Presevation Attenuates Ischemia/Reperfusion Markers After Liver Transplantation: Preliminary Results," Journal of Surgical Research., May 2011, vol. 167, Issue 2, pp. e365-e373 (Abstract).
Houghten, et al., "The Use of Synthetic Peptide Combinatorial Libraries for the Identification of Bioactive Peptides," Biotechniques, Sep. 1992, vol. 13, No. 3, pp. 412-421 (Abstract).
Jamieson et al., "Hepatic Steatosis and Normothermic Perfusion-Preliminary Experiments in a Porcine Model," Transplantation, Aug. 2011, vol. 92, No. 3, pp. 289-295 (Abstract).
Lam, et al., "Letters to Nature: A New Type of Synthetic Peptide Library for Identifying Ligand-Binding Activity," Nature, Nov. 1991, vol., pp. 82-84.
Lam, "Application of Combinatorial Library Methods in Cancer Research and Drug Discovery," Anticancer Drug Des., Apr. 1997, vol. 12, No. 3, pp. 145-167 (Abstract).
Maguire et al., "Alginater-PLL Microencapsulation: Effect on the Differentiation of Embryonic Stem Cells Into Hepatocytes," Biotechnology and Bioengineering, Feb. 2006, vol. 93, No. 3, pp. 581-591.
Mokuno et al., "Technique for Expanding the Donor Liver Pool: Heat Shock Preconditioning in a Rat Fatty Liver Model," Liver Transplantation, Feb. 2004, vol. 10, No. 2, pp. 264-272.
Nagrath et al., "Metabolic Preconditioning of Donor Organs: Defatting Fatty Livers by Normothermic Perfusion Ex Vivo," Metabolic Engineering, 2009, vol. 11, No. 4-5, pp. 274-283.

Nakamuta et al., "Short-Term Intensive Treatment for Donors With Hepatic Steatosis in Living-Donor Liver Transplantation," Transplantation, Sep. 2005, vol. 80, No. 5, pp. 608-612 (Abstract).
Nativ et al., "Liver Defatting: An Alternative Approach to Enable Steatotic Liver Transplantation," American Journal of Transplantation, Dec. 2012, vol. 12, No. 12, pp. 3176-3183 (Abstract).
Ninomiya et al., "Sustained Spatial Disturbance of Bile Canalicular Networks During Regeneration of the Steatotic Rat Liver," Transplantation, Feb. 2004, vol. 77, No. 3, pp. 373-379 (Abstract).
Pontoglio et al., "Hepatocyte Nuclear Factor 1 Inactivation Results in Hepatic Dysfunction, Phenylketonuria, and Renal Fanconi Syndrome," Cell, Feb. 1996, vol. 84, pp. 575-585.
Scott and Smith, "Searching for Peptide Ligands With an Epitope Library," Science, Jul. 1990, vol. 249(4967), pp. 386-390 (Abstract).
Selzner et al., "Mouse Livers With Macrosteatosis are More Susceptible to Normothermic Ischemic Injury Than Those With Microsteatosis," J of Hepatol, Apr. 2006, vol. 44, No. 4, pp. 694-701, e-published Sep. 2005 (Abstract).
Serafin et al., "Ischemic Preconditioning Increases the Tolerance of Fatty Liver to Hepatic Ischemia-Reperfusion Injury in the Rat," Am J Pathol, Aug. 2002, vol. 16, No. 2, pp. 587-601.
Spitzer et al., "The Biopsied Donor Liver: Incorporating Macrosteatosis Into High-Risk Donor Assessment," Liver Transpl, Jul. 2010, vol. 16, No. 7, pp. 874-884.
Taneja et al., "Critical Preservation Injury in Rat Fatty Liver is to Hepatocytes, Not Sinusoidal Lining Cells," Transplantation, Jan. 1998, vol. 65, No. 2, pp. 167-172 (Abstract).
Tuschl et al., "Serum-Free Collagen Sandwich Cultures of Adult Rat Hepatocytes Maintain Liver-Like Properties Long Term: A Valuable Model for in Vitro Toxicity and Drug-Drug Interaction Studies," Chemico-Biological Interactions, Sep. 2009, vol. 181, No. 1, pp. 124-137 (Abstract).
Vairetti et al., "Subnormothermic Machine Perfusion Protects Steatotic Livers Against Preservation Injury: a Potential for Donor Pool Increase?," Liver Transplantation, Jan. 2009, vol. 15, No. 1, pp. 20-29.
Washizu et al., "Amino Acid Supplementation Improves Cell-Specific Functions of the Rat Hepatocytes Exposed to Human Plasma," Tissue Engineering, Oct. 2000, vol. 6, No. 5, pp. 497-504 (Abstract).
Wiggins and Gibbons, "The Lipolysis/Esterification Cycle of Hepatic Triacylglycerol," Biochem J., 1992, vol. 284, pp. 457-462.
Zuckermann et al., "Discovery of Nanomolar Ligands for 7-Transmembrane G-Protein-Coupled Receptors from a Diverse N-(Substituted)glycine Peptoid Library," J. Med Chem, Aug. 1994, vol. 37, No. 17. pp. 2678-2685.
Han et al., Microsteatosis may not interact with macrosteatosis in living donor liver transplantation, Journal of Hepatology (2015); 62:556-562.
Han et al., "Effect of pure Microsteatosis on Transplant Outocmes After Living Donor Liver Transplantation: A Matcehd Case-Control Study," Liver Transplantation (2014); 20-473-482.
Nativ et al., "Automated Image Analysis Method for Detecting and Quantifying Macrovesicular Steatosis in Hematoxylin and Eosin-Stained Histology Images of Human Livers," Liver Transplantation (2014); 20:228-236.
Nativ et al., "Rat hepatocyte culture model of macrosteatosis: Effect of macrosteatosis induction and reversal on viability and liver-specific function," Journal of Hepatology (2013); 59:1307-1314.
Orlicky et al., "Chronic Ethanol Consumption in Mice Alters Hepatocyte Lipid Droplet Properties," Alcoholism: Clincial and Experimental Research (Jun. 2011); 35(6):1020-1033.
Willebrords et al., "Strategies, models and biomarkers in experimental non-alcoholic fatty liver disease research," Progress in Lipid Research (2015); 55:106-125.

* cited by examiner

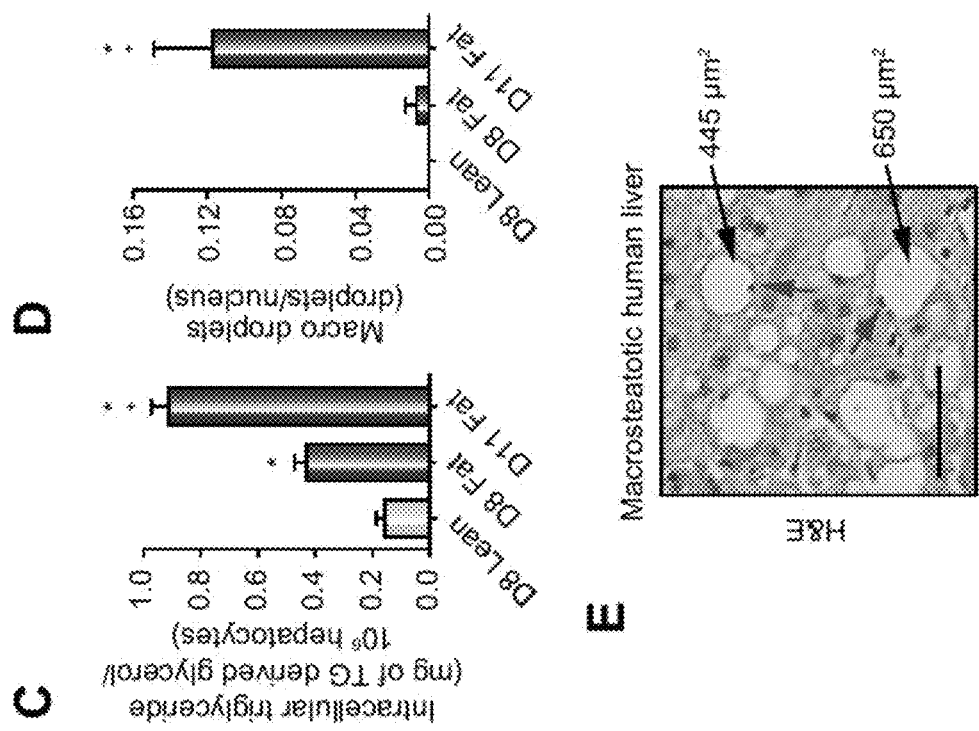
FIGs. 1C, 1D, and 1E

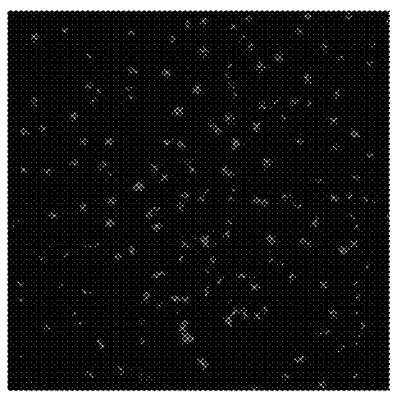
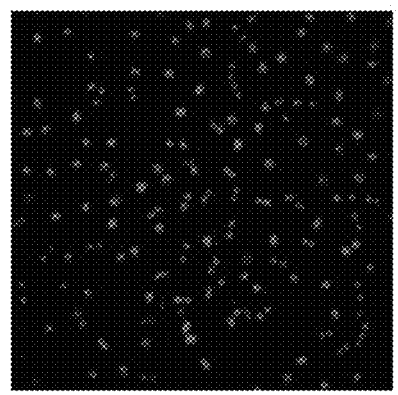
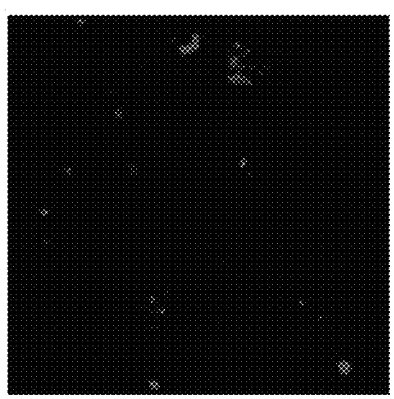
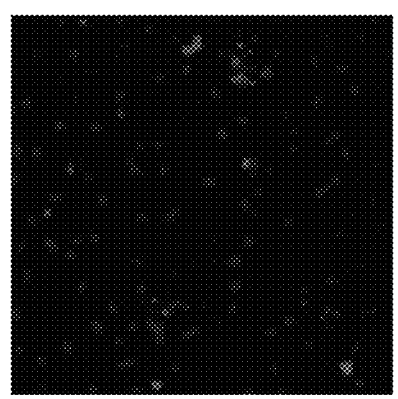
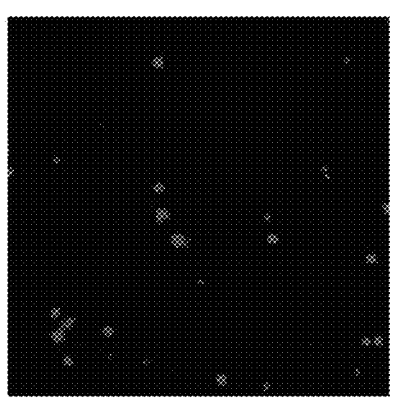
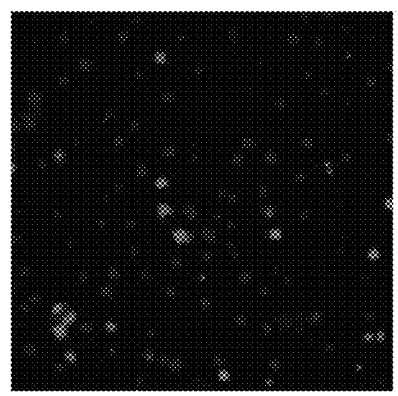
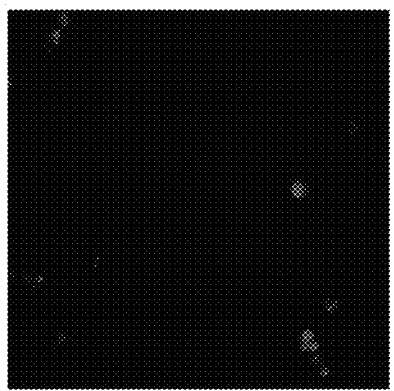
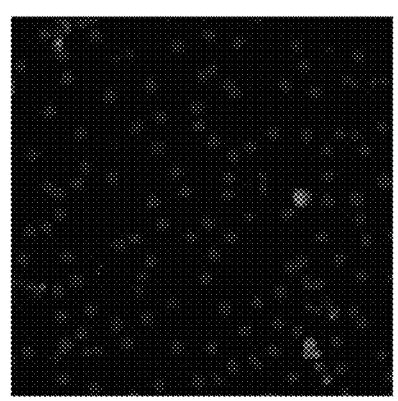
FIG. 5 – continued

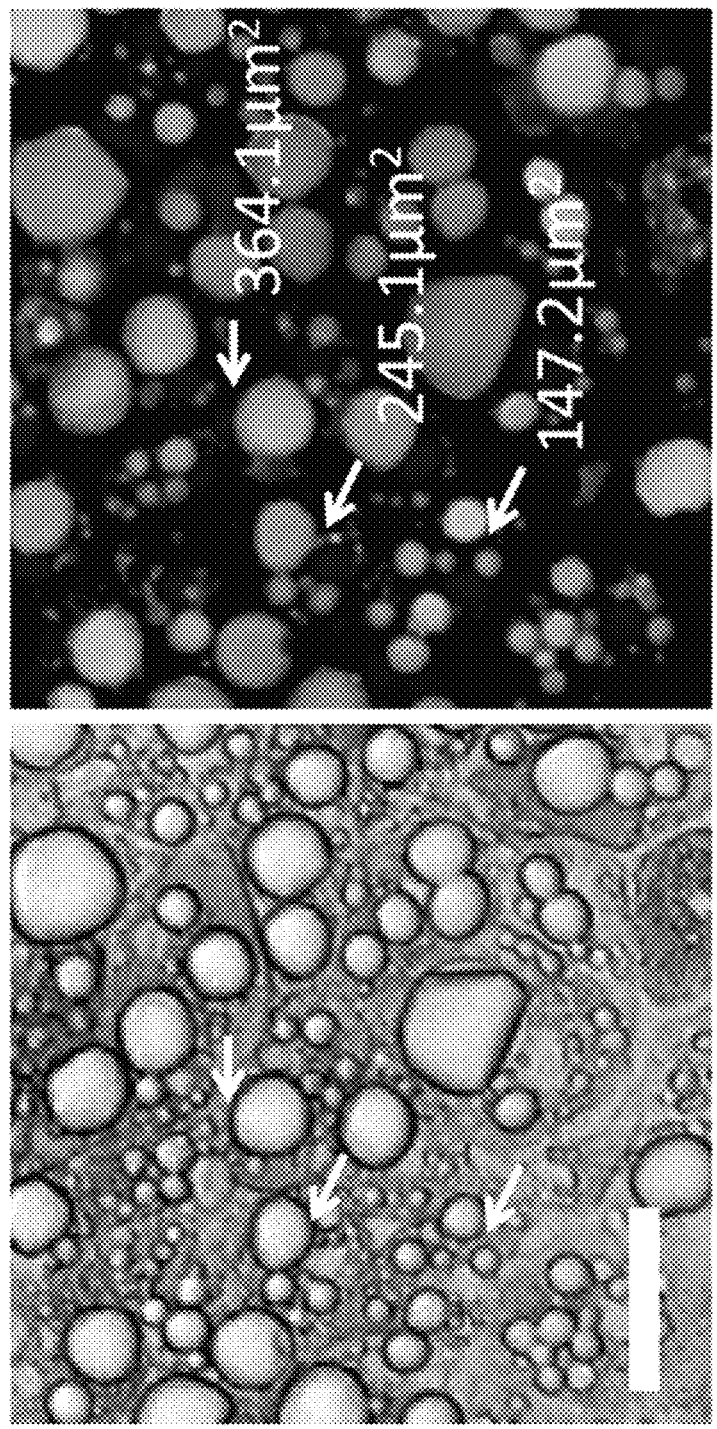
FIGS. 6A-B

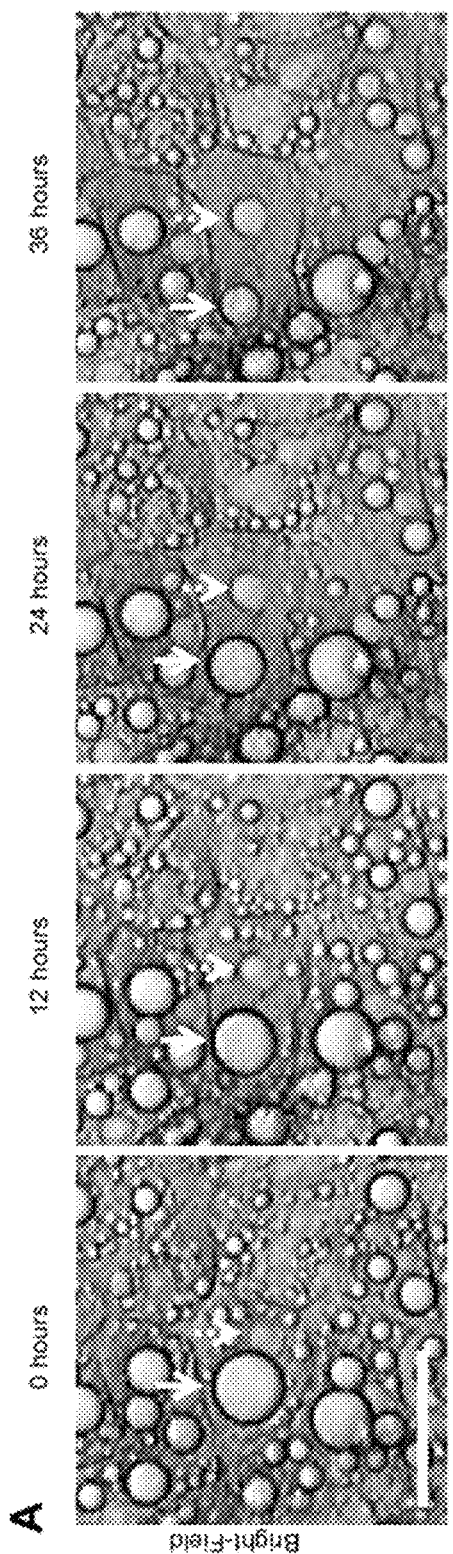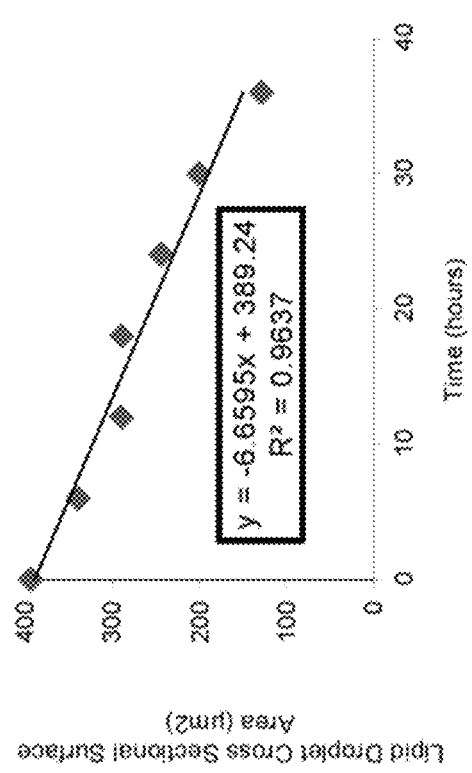
FIGS. 7A-B

| Amino acids | Concentration (mg/L) |
|---|---|
| L-Arginine hydrochloride | 252.8 |
| L-Cystine | 48 |
| L-Histidine hydrochloride-H2O | 84 |
| L-Isoleucine | 104.8 |
| L-Leucine | 104.8 |
| L-Lysine hydrochloride | 146 |
| L-Methionine | 30.2 |
| L-Phenylalanine | 66 |
| L-Threonine | 95.2 |
| L-Tryptophan | 20.4 |
| L-Tyrosine | 72 |
| L-Valine | 93.6 |
| Glycine | 30 |
| L-Alanine | 35.6 |
| L-Asparagine | 52.8 |
| L-Aspartic acid | 53.2 |
| L-Glutamic Acid | 58.8 |
| L-Proline | 46 |
| L-Serine | 42 |
| L-Glutamine | 584 |

FIG. 8

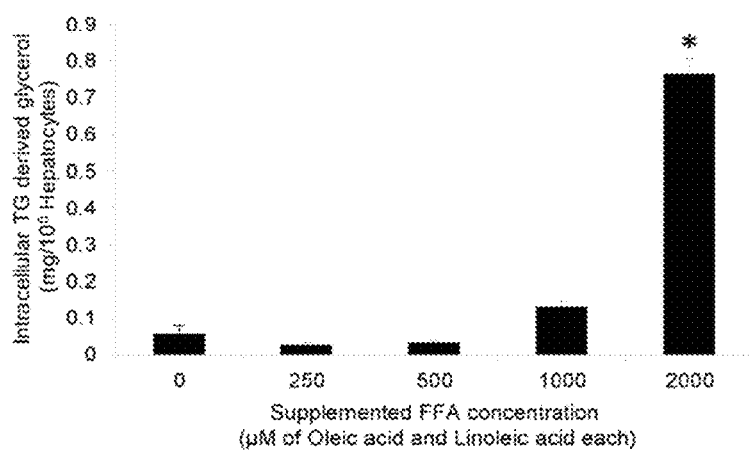
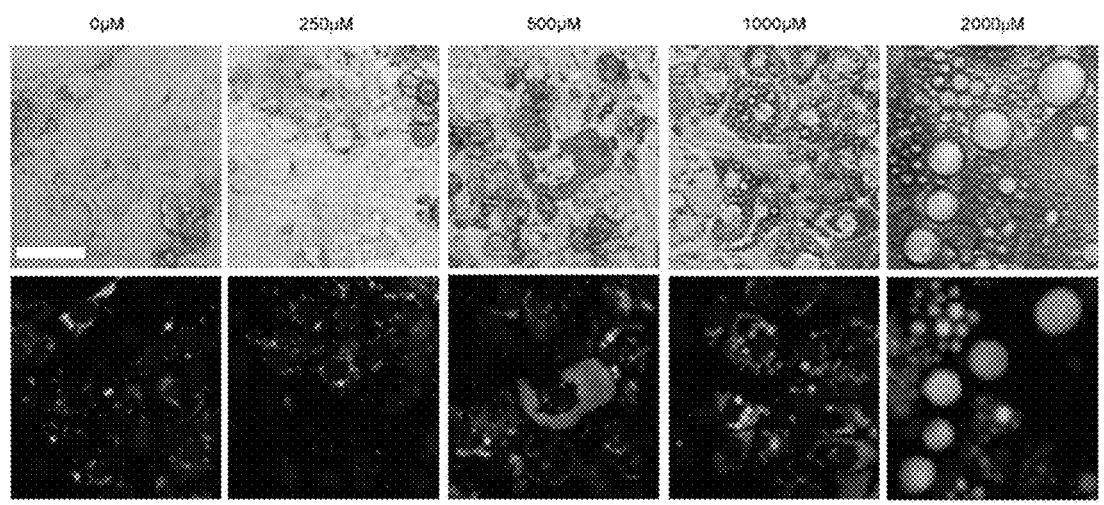
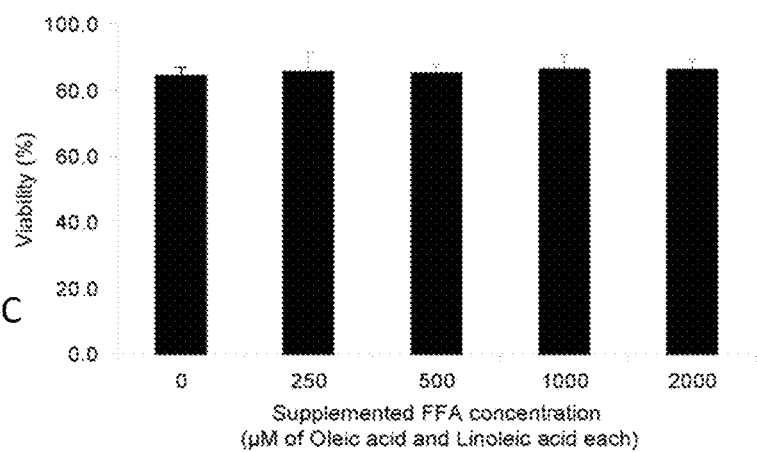
FIGS. 9A-C ion No. 61/759,113 filed on Jan. 31, 2013. The content of
IN VITRO MODEL OF MACROSTEATOTIC (FATTY) LIVER

CROSS REFERENCE TO RELATED APPLICATION

This application claims priority of U.S. Provisional Application No. 61/759,113 filed on Jan. 31, 2013. The content of the application is incorporated herein by reference in its entirety.

GOVERNMENT INTERESTS

The invention disclosed herein was made, at least in part, with Government support under Grant No. R01DK059766 and UH2 NS080733 from the National Institutes of Health. Accordingly, the U.S. Government has certain rights in this invention.

FIELD OF THE INVENTION

This invention relates to a system and methods for identifying compounds or agents for de-fatting and functional recovery of macrosteatotic hepatocytes. This system enables identifying key hepatic intracellular pathways, which govern the pathology of non-alcoholic fatty liver disease.

BACKGROUND OF THE INVENTION

The liver is a vital organ in various vertebrates and some other animals. In the human body, the liver is the largest internal organ, providing many essential functions, including metabolic, exocrine and endocrine functions. The liver is necessary for survival as without liver function a human can only survive up to 24 hours. Disorders of the liver, including liver failure and end-stage liver diseases, are responsible for a large number of deaths around the world and are a major burden on the health care system. Based on the organ procurement and transplantation network (OPTN), transplantation of whole liver from cadaveric donors was shown to be effective in saving the lives of about 7,000 patients who receive such livers annually in the U.S. However, about 16,000 patients remain untreated on the waiting list annually. This shortage of suitable livers leads to about 4,000 death in the US alone.

A common reason of liver donor ineligibility is excessive fat content, known as macrosteatosis, which is characterized by the presence of large lipid droplets inside the parenchymal cells of the liver, hepatocytes. Furthermore, these droplets displace the nuclei to the cell periphery. Methods to recover such livers could enhance donor availability. One such method that has been proposed is to subject these livers to machine perfusion in the presence of compounds that promote accelerated lipid droplet breakdown and metabolism. However, a thorough exploration of such compounds, and combinations thereof, is necessary to achieve "de-fatting" of the livers in a timescale of a few hours.

Thus, there is a need for systems and methods for identifying compounds or agents for de-fatting and functional recovery of macrosteatotic hepatocytes.

SUMMARY OF INVENTION

This invention relates to a system and methods for identifying compounds or agents for de-fatting and functional recovery of macrosteatotic hepatocytes.

In one aspect, the invention provides an in vitro culture system having a cell population containing cultured or isolated macrosteatotic hepatocytes and a culture medium. In one embodiment, the culture system is an in vitro co-culture system that includes macrosteatotic hepatocytes and additional cells, such as fibroblasts, normal hepatocytes, Kupffer cells, other combinations of livers cells, or cells from non-liver organs.

Preferably, a substantial portion (e.g., more than about 50, 60, 70, 80, 90, 95, or 99%) of the population are macrosteatotic hepatocytes. The macrosteatotic hepatocytes can be maintained in a collagen matrix such as a collagen matrix in a sandwich configuration and other matrixes such as Matrigel™. The macrosteatotic hepatocytes can be derived from an animal, including a human or a non-human mammal, such as a rodent (e.g., a rat or mouse).

In the culture system, the macrosteatotic hepatocytes can contain lipid macrodroplets or contain a higher (e.g., about 2, 3 or 4 times) amount of triglyceride as compared to control normal hepatocytes. The culture medium can be one selected from the group consisting of a standard medium, a steatosis inducing medium, and a steatosis reducing medium as disclosed herein.

In a second aspect, the invention provides a screening method of identifying a compound or composition for de-fatting and functional recovery of macrosteatotic hepatocytes. The method includes the following steps: obtaining a first culture system described above, which has a population of cultured macrosteatotic hepatocytes; incubating the macrosteatotic hepatocytes in a test medium containing a test compound or test composition for a first period of time; and determining a macrosteatosis level or a function level of the macrosteatotic hepatocytes. The test compound is determined as being effective for de-fatting and functional recovery of macrosteatotic hepatocytes if (i) the macrosteatosis level is lower than a control macrosteatosis level (e.g., by about 10%, 20%, 30%, 40%, 50%, 60%, 70%, 80%, or more) or (ii) the function level is higher than a control function level (e.g., by about 10%, 20%, 30%, 40%, 50%, 60%, 70%, 80% or more), or both. The control macrosteatosis or function level can be determined in the same manner from a second culture system obtained and incubated in the same manner as the first culture system except that the second system is incubated in a control medium free of the test compound. In one embodiment, the macrosteatosis level can be selected from the group consisting of a level of lipid macrodroplets (e.g., sizes of lipid droplets or an average thereof) and a level of triglyceride as well as secreted products indicating defatting (e.g., secreted triglyceride in the form of very low density lipoprotein, VLDL or secreted ketone molecules which indicate hepatic fat oxidation). In addition, macrosteatotic hepatocytes are defined as containing large lipid droplets that can displace the nucleus to the periphery of the hepatocyte cytoplasm. Therefore, reversing this nucleus displacement by the lipid droplets following defatting, can be an indicator of macrosteatosis defatting. The functional level can be selected from the group consisting of a level of urea secretion (e.g., urea secretion rate in terms of $\mu g/10^6$ cells/day) and a level of bile canalicular function, which can be determined by e.g., examining carboxy-DCFDA accumulation and morphology as described below. In the method, the first period of time can be about 2 hours to about 3 days, such as 2 days. The method can further include, after the first period of time, culturing the macrosteatotic hepatocytes in a standard medium for a second period of time. The second period of time can be about 2 hours to about 3 days (e.g., about 2 days). The above-mentioned time scale of days in a static culture system is equivalent to only several hours in a perfusion system (Nagrath et al. Metabolic Engineering. 11(4-5):274-83).

In yet another aspect, the invention features a method of producing a population of cultured macrosteatotic hepatocytes described above. The method includes providing a population of hepatocytes; culturing the population of hepatocytes on a collagen matrix for a first period of time; distributing a collagen gel solution over the hepatocytes to create a collagen sandwich configuration so that the hepatocytes are in the middle of the collagen sandwich configuration; culturing the hepatocytes in the collagen sandwich configuration for a second period of time; culturing the hepatocytes in a steatosis inducing medium for a third period of time to obtain a population of cultured macrosteatotic hepatocytes. The first period of time can be about 12 hours to 48 hours (e.g., about 18-30 hours or about 24 hours). The second period of time can be about 2 days to 3 weeks (e.g., about 3-5 days or about 4 days). The third period of time can be about 3-9 days, e.g., about 5-7 days or about 6 days, depending on the concentration of the steatosis inducing agent in the medium.

In another aspect, the invention enables exploring key regulatory pathways in the pathological state of non-alcoholic fatty liver disease (NAFLD), which is characterized by macrosteatosis. This can be used to identify lead to therapies to reverse NAFLD by de-fatting the livers and prevent its progression to nonalcoholic steatohepatitis (NASH).

The details of one or more embodiments of the invention are set forth in the description below. Other features, objectives, and advantages of the invention will be apparent from the description and from the claims.

BRIEF DESCRIPTION OF THE DRAWINGS

FIGS. 1A-E are diagram and photographs showing macrosteatosis induction in primary rat hepatocytes: A. Experimental timeline. B. Hepatocyte morphology post-free fatty acids (FFA)-supplemented culture. Bright-field (top) and fluorescent images of Nile red and Hoechst stained hepatocytes (bottom) for lean (day 8), microsteatotic (day 8), and macrosteatotic hepatocytes (day 11). White arrows=lipid droplets and cross-sectional areas. Red arrows=hepatocyte nuclei. C, D. Intracellular TG content and macrosteatotic (>350 μm$^2$) droplet number as a function of steatosis. Means±S.E. N=6. *p<0.002 vs. D8 Lean, $^+$p<0.007 vs. D8 Fat. E. H&E-stained human steatotic liver. Arrows=macrovesicular lipid droplets and cross-sectional surface areas. Bars=50 μm.

FIGS. 6A-B are bright-field (A) and H&E-staining (B) photographs showing lipid droplet minimal cross-sectional surface area defining macrosteatosis. Lipid droplet sizes were measured within hepatocyte cultures exposed to steatosis inducing medium for 6 days. A survey of individual cells revealed that nuclear dislocation to the cell periphery occurred when the cross-sectional surface area of lipid droplets reached 350 μm2. Shown is a representative image of hepatocyte cultures showing lipid droplet sizes and nuclear location. Bar=50 μm.

FIGS. 7A-B are a set of photographs and a diagram showing morphological changes of representative lipid droplets during macrosteatosis reduction: A. Bright-field time lapse images of macrosteatotic hepatocytes during the first 36 h in SRS medium. Solid arrows=a single macrovesicular droplet; dashed arrows=nucleus in the same cell. The image sequence shows shrinking of the lipid droplet and return of the nucleus to the center. Bar=50 μm. B. Cross sectional surface area of the lipid droplet visualized in panel A decreases linearly with time.

FIG. 8 is a table showing supplemented amino acids supplemented to steatosis reducing culture medium (SRS) and respective concentrations (mg/L).

FIGS. 9A-C are a set of photographs and a diagram showing effect of FFA concentration on steatotic induction. Hepatocyte cultures were incubated for 6 days (Days 5-11 post-seeding with one media change at day 8 post-seeding) in standard hepatocyte culture medium supplemented with 0, 250, 500, 1000 or 2000 μM of oleic acid and the same concentration of linoleic acid. A. Intrahepatic TG for these cultures on day 11 post-seeding. *p<0.05 vs. 0 μM. B. Representative bright-field images (top), Nile red (green), and Hoechst (blue) stained cultures (bottom). Bar=50 μm. C. Hepatocyte percent viability in each of the cultures as assessed by EHD-1 assay. P=0.99 indicating no significant difference among the conditions. Means±S.E. N=5.

DETAILED DESCRIPTION OF THE INVENTION

Figure 1A:
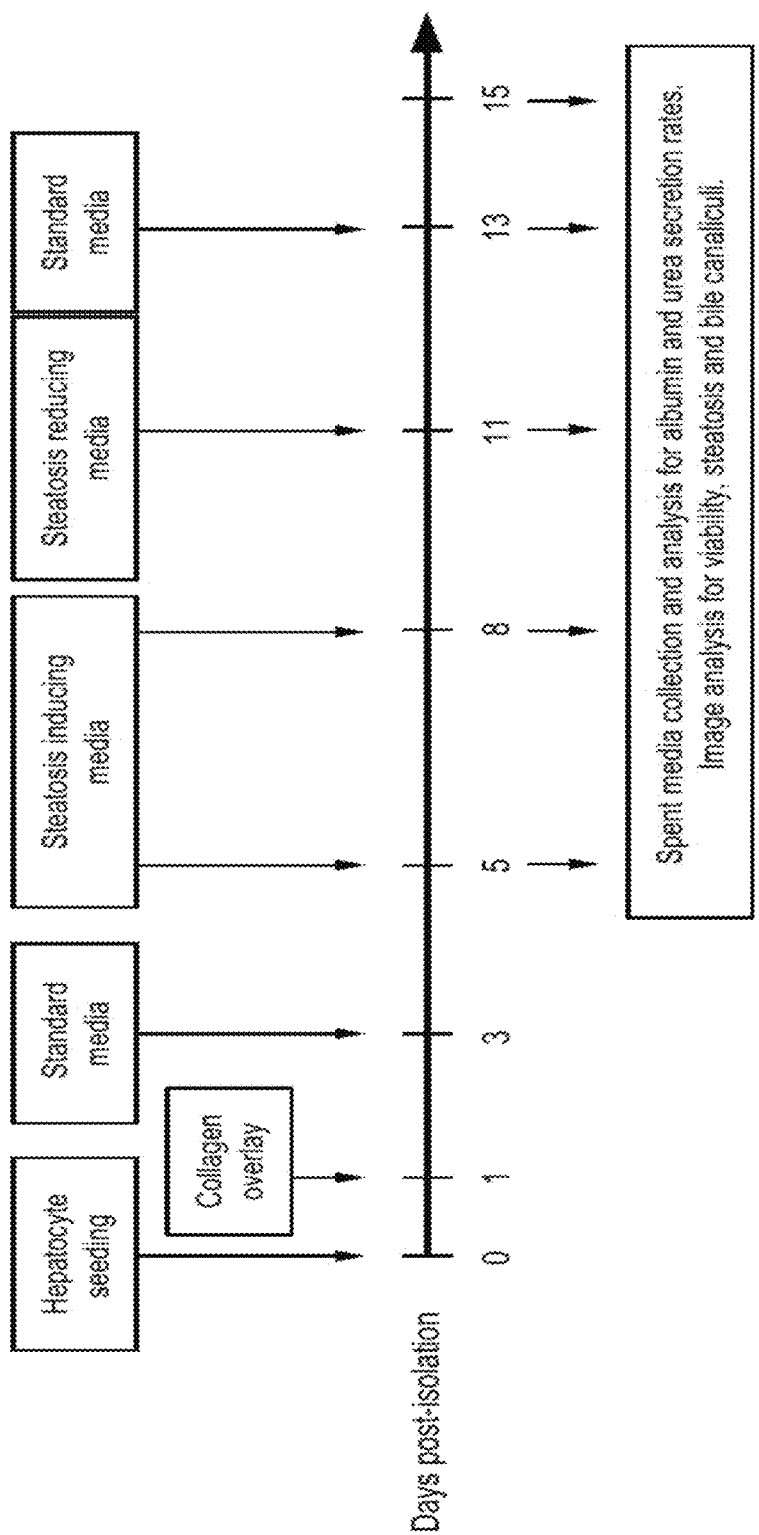

This invention is based, at least in part, on unexpected discoveries that macrosteatotic hepatocytes can be generated and maintained in vitro and that steatosis reduction can be induced in vitro in cultured macrosteatotic hepatocytes in a short term. It is also based on the discoveries that macrosteatosis reversibly decreases hepatocyte function and that supplementary agents accelerate macrosteatosis reduction and some functional restoration with no deleterious effect on viability of hepatocytes.

Accordingly, in one aspect, the invention provides a model system in which macrosteatosis can be induced by culturing hepatocytes in FFA-rich medium. This model is suitable to explore the effect of macrosteatosis reduction approaches on lipid droplet size as well as hepatocyte viability and liver-specific function. Macrosteatotic hepatocyte cultures maintain high viability but decreased function. Accelerated macrosteatosis reduction does not adversely affect viability and accelerates some functional restoration. This system is useful to improve the understanding of the effect of macrosteatosis on lipid metabolism and storage, liver-specific functions and hepatocellular response to stresses, such as ischemia/reperfusion (I/R) or its static in vitro culture equivalent, hypoxia/reoxygenation (H/R).

This model can also serve as platform to screen and test various lipid metabolism promoting agents that could eventually be used to reduce macrosteatosis in human livers. To that end, this model can be used in conjunction with other methods, such as I/R preconditioning and/or anti-oxidant-based methods to expand the liver donor pool (Nativ et al., American Journal of Transplantation. 2012; Serafin et al., The American Journal of Pathology. 2002; 161(2):587-601; Mokuno et al., Liver Transplantation. 2004; 10(2):264-72; and Vairetti et al. Liver Transplantation. 2009; 15(1):20-9).

In addition, this in vitro macrosteatotic hepatocyte model is useful to screen agents for macrosteatotic reduction in donor livers before transplantation. As mentioned above, orthotopic liver transplantation is severely limited by donor scarcity. This has motivated the development of strategies to recover livers from deceased donors currently not considered suitable for transplantation. Macrosteatosis, defined as the accumulation of triglycerides (TG) in the form of large lipid droplets that displace the nucleus to the cell periphery, when found in more than 30% of the hepatocytes, is a very common cause of donor ineligibility (de Graaf et al. J Gastroenterol Hepatol. 2012 March; 27(3):540-6 and Spitzer et al. Liver Transpl. 2010 July; 16(7):874-84). Such livers are more sensitive to I/R injury inherent to liver transplantation, and more prone to primary non-function, as well as increased morbidity and mortality post-transplantation. The incidence of hepatic macrosteatosis is likely to surge due to the obesity epidemic. Thus, techniques to salvage macrosteatotic livers could significantly enhance donor supply in both the short and long terms.

A variety of approaches targeting the downstream effects of macrosteatosis during I/R have shown promise in preclinical and clinical settings. However, several studies suggest that excessive hepatic lipid storage is a primary cause of the exuberant I/R response, especially when in the macrosteatotic form. Therefore, an alternative approach could be to eliminate the intracellular lipid droplets, thus decreasing the frequency of macrosteatotic hepatocytes below acceptable levels. Dieting, exercise, and fibrate drugs over several weeks have been shown to decrease macrosteatosis and enable living donor liver transplantation. In a rat liver model of macrosteatosis (induced by a choline and methionine-deficient diet; CMDD), switching to a normal diet 3 days prior to transplantation reduced intrahepatic TG content by 35% and increased recipient viability from 0% to >75% post-transplantation (Berthiaume et al., Journal of Surgical Research. 2009; 152(1):54-60).

Diet/drug-induced macrosteatosis reduction occurs over days to weeks, a timescale that is not applicable to deceased human donors, which would require macrosteatotic reduction ex vivo within a few hours. Animal studies have demonstrated the feasibility of macrosteatosis reduction via machine perfusion of explanted steatotic livers. This process was accelerated by introducing agents that promote lipid metabolism (Jamieson et al. Transplantation. 2011; 92(3):289-95; Nagrath et al. Metabolic Engineering. 11(4-5):274-83; and Vairetti et al. Liver Transplantation. 2009; 15(1):20-9). However, a thorough exploration of such agents and combinations thereof, has yet to be performed. Furthermore, there has been little investigation of the impact of accelerated macrosteatosis reduction on the viability and function of hepatocytes, parameters that are critical for the successful outcome of liver transplantation.

The cell culture model disclosed herein can be used to facilitate the evaluation of these agents with the ultimate goal of developing protocols to promote accelerated macrosteatosis reduction and functional recovery of transplanted steatotic livers. Microsteatotic hepatocyte culture systems have been described in this context in the literature; however, their relevance is unclear given that clinical evidence suggests that macrosteatotic—and not microsteatotic—livers are hypersensitive to I/R. As disclosed herein, a novel macrosteatotic hepatocyte culture system is provided to investigate the effect of macrosteatosis on viability and liver-specific functions in hepatocytes.

As shown in the examples below, this system was successfully used to explore the impact of accelerated macrosteatosis reduction on viability and the recovery of such functions. More specifically, a novel in vitro primary rat macrosteatotic hepatocyte system was characterized whereby intracellular TG accumulation and macrosteatotic lipid droplet formation were induced by incubation in FFA-rich medium. It was found that macrosteatosis induction did not decrease hepatocyte viability, but significantly decreased urea secretion, disrupted the bile canalicular network, and maintained albumin secretion rates below lean controls. Macrosteatosis was morphologically reversed by switching hepatocytes back to NSRS medium within, e.g. 4 days. Comparable macrosteatosis reduction was achieved in only 2 days with SRS medium. Hepatocyte viability remained high and did not depend on the macrosteatosis reduction rate. Macrosteatosis reduction led to the recovery of liver-specific functions at different rates. Using the SRS medium, urea secretion and the bile canalicular network fully recovered, while albumin secretion rate remained flat and below control lean hepatocyte levels during the macrosteatosis reduction experimental 4-day timeframe. Since some aspects of hepatocyte functional recovery were improved by accelerated macrosteatosis reduction, this recovery may be dependent upon macosteatosis reduction time and/or may be sensitive to the composition of the supplements and their target pathways.

The study disclosed herein indicates that macrosteatosis significantly decreased bile canalicular function, consistent with observations made post 70% partial hepatectomy in a CMDD rat macrosteatotic liver model, where the recovery of the bile canalicular network was significantly delayed. During recovery, the animals were given a normal diet, which is expected to reduce the steatosis level to that of lean animals (Berthiaume et al., Journal of Surgical Research. 2009; 152(1):54-60; and Ninomiya et al., Transplantation. 2004; 77(3):373-9). In addition, steatotic rat liver perfusion studies indicate an increased bile secretion rate post-steatosis reduction (Nagrath et al. Metabolic Engineering. 11(4-5):274-83; Vairetti et al. Liver Transplantation. 2009; 15(1): 20-9). Therefore, the steatosis reduction process could have contributed to some aspects of functional recovery of macrosteatotic hepatocytes.

As disclosed herein, addition of SRS significantly reduced lipid droplet size compared to NSRS, but TG content was reduced to the same level using either media composition. This contrasts with prior studies using microsteatotic hepatocyte cultures, where SRS promoted a higher degree of TG reduction compared to NSRS medium (Nagrath et al. Metabolic Engineering. 11(4-5):274-83). The macrosteatotic culture system, which contains 2-fold higher TG levels compared to the microsteatotic system, may have impaired ability to eliminate lipolysis products from the cytoplasm, allowing their re-esterification to TG stored in small lipid droplets, which may not be detectable using the Nile red stain method (Nagrath et al. Metabolic Engineering. 11(4-5):274-83; and 22. Gibbons et al., Biochem J. 1992; 284(Pt 2):457-62. If this is the case, further improvement in TG removal can be achieved by preventing TG re-esterification, which would also help elucidate whether the redistribution of TG from macro- to micro-droplets, or its removal from the cell altogether, is required (Nir et al., American Journal of Transplantation. 2012).

The above-described accelerated macrosteatosis reduction strategies can be used and consequently recover some liver-specific function. The macrosteatosis reduction time scale was ~48 h to reduce the number of macrodroplets by ~80%. In order to clinically translate this approach to liver grafts, this would need to be accomplished in a few hours. Interestingly, one study showed that ex vivo perfusion of obese Zucker rat steatotic liver with a similar cocktail could achieve a significant reduction in lipid droplet size as well as 50% TG reduction within 3 h (Nagrath et al. Metabolic Engineering. 11(4-5):274-83; and Maguire et al., Biotechnology and Bioengineering. 2006; 93(3):581-91). Thus, it is possible that faster dynamics occur in perfused livers, possibly due to the flow conditions, which likely enhance nutrient and waste transport between cells and the bathing medium (Nir et al., American Journal of Transplantation. 2012). To further improve the macrosteatotic hepatocyte culture model, one can introduce a flow component, thus enabling a more rigorous analysis of the combined effects of lipid metabolism promoting agents and flow parameters on the macrosteatosis reduction process (Nir et al., American Journal of Transplantation. 2012).

As disclosed herein, the invention provides an in vitro model for liver macrosteatosis. This system can be used to screen defatting agents for fat cells, adipocytes or to identify improved diets or drugs to reduce body fat content in the contexts of obesity. This system contains cells derived from starting cells, such as hepatocytes, hepatocyte-like cells, or their progenitor cells known in the art. Hepatocyte-like cell refers to a cell displaying one or more properties that are characteristic of mature, parenchymal hepatocytes. In general, a hepatocyte-like cell may display at least one, two, three, four, five or more of the following properties: ability to use pyruvate as a sole carbon source; phase I biotransformation capacity (e.g. ethoxyresorufin, pentoxyresorufin, testosterone); phase II biotransformation capacity (e.g. 1-chloro-2,4 dinitrobenzene, 1,2-dichloro-4-nitrobenzene, 7-chloro-4-nitrobenzene-2-oxa-1,3-diazole, estradiol, estrogen), the presence of cytochrome P450 protein and gene expression; inducibility of phase I and phase II biotransformation enzymes (e.g. β-naphthoflavone, phenobarbital, methylcholanthrene); albumin secretion, urea production, fibrinogen secretion, glycogen storage, the presence of the expression of one or more of endogenous ALB, AFP, gamma-glutyryltransferase, hepatocyte nuclear factor (HNF) 1α, HNF 1β, HNF 3α, HNF 3β, HNF 4, HNF-6, anti-trypsin, CX32, MRP2, C/EBPα, transthyretin, CK-18 and/or CFTR; polygonal morphology.

Various cells from a subject or animal can be used as the starting cells. In some embodiments, the starting cells are stem cells. The stem cells useful for the method described herein include but not limited to embryonic stem cells, mesenchymal stem cells, bone-marrow derived stem cells, hematopoietic stem cells, chondrocyte progenitor cells, epidermal stem cells, gastrointestinal stem cells, neural stem cells, hepatic stem cells, adipose-derived mesenchymal stem cells, pancreatic progenitor cells, hair follicular stem cells, endothelial progenitor cells, and smooth muscle progenitor cells. The stem cells can be pluripotent or multipotent. In some embodiments, the stem cell is an adult, fetal or embryonic stem cell. The stem cells can be isolated from umbilical, placenta, amniotic fluid, chorion villi, blastocysts, bone marrow, adipose tissue, brain, peripheral blood, blood vessels, skeletal muscle, and skin. To convert stem cells to hepatocytes or hepatocyte-like cells, one needs to induce the stem cells so that they differentiate. Various methods were known in the art for achieving this purpose. See, e.g., WO2011102532, WO2012058868, US20090191159, US20110070647, US2011004260, and US20120244129.

In a preferred example, starting cells are hepatocytes. To that end, hepatocytes can be isolated from a suitable animal (e.g., lean Zucker rats) and maintained in a standard medium. To induce steatosis, the hepatocytes can then be cultured in a collagen sandwich and incubated for about 3-9 days (e.g., 5-7 days or 6 days) in a fatty acid-supplemented medium (i.e., a steatosis inducing medium). The cultured cells can then be switched for 4 hours-6 days (e.g., 2 days) to a medium supplemented with lipid metabolism promoting agents (i.e., steatosis reducing medium). During this period, intracellular lipid droplet size distribution and triglyceride, viability, albumin and urea secretion and bile canalicular function can be measured in the manner described in the example below or using methods known on the art. Generally, the fatty acid-supplemented medium should induce microsteatosis in about 3 days and macrosteatosis in about 6 days, with the latter evidenced by large lipid droplets dislocating the nucleus to the cell periphery.

As used herein, the term "a large lipid droplet" refers to an intracellular, triglyceride-containing droplet of a hepatocyte, where the area of such a droplet is about 200 $\mu m^2$-2000 $\mu m^2$, for example 350 or above, such as 350-2000 $\mu m^2$ as determined by a non-destructive quantitative image analysis method in the manner described in the example section below.

As used herein, a standard medium or standard hepatocyte medium refers to any medium that can be used to culture or maintain hepatocytes without causing phenotype changes. Examples of the standard medium include DMEM, C+H, Williams Medium E, HCM™ Hepatocyte Culture Medium, HMM™ Hepatocyte Maintenance Medium, InVitroGRO™ Hepatocyte Media and others known in the art. A steatosis inducing medium is identical to a standard medium except that it contains one or more steatosis induction agents, e.g., fatty acids such as oleic acid, linoleic acid, and palmatic acid with bovine serum albumin (BSA) as fatty acid carrier, insulin and glucose at high concentrations, and heparinized plasma, which is high in free fatty acids. A steatosis reducing medium is identical to a standard medium except that it contains one or more steatosis reduction supplements. A reduction supplement or agent refers to any agent that increases lipid oxidation (for example mitochondrial beta-oxidation) or lipid export (for example via secretion of VLDL particles), such as forskolin, GW7647, scoparone, GW501516, hypericin, visfatin, and amino acids as well as bile acids.

The term "animal" includes all vertebrate animals including humans. It also includes an individual animal in all stages of development, including embryonic and fetal stages. In particular, the term "vertebrate animal" includes, but not limited to, humans, non-human primates (particularly higher primates), canines (e.g., dogs), felines (e.g., cats); equines (e.g., horses), bovines (e.g., cattle), porcine (e.g., pigs), rodent (e.g., mouse or rat), guinea pig, cat, rabbit, as well as in avians, such as birds, amphibians, reptiles, etc. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary. Examples of a non-human animal include all non-human vertebrates, e.g., non-human mammals and non-mammals mentioned above.

The invention provides a method of identifying a compound or a composition for de-fatting and functional recovery of macrosteatotic hepatocytes. The compound/composition thus-identified can be used to promote accelerated lipid droplet breakdown and metabolism in liver tissue as well as reduce the cell's and or the graft's sensitivity to ischemia/reperfusion injury associated with liver procurement and transplantation.

Candidate compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a compound or composition mentioned above, one can contact or incubate a candidate compound or composition with the system disclosed herein. The cells can be macrosteatotic hepatocytes derived from normal, lean hepatocytes as described in the example below. After the incubation, one then measures macrosteatosis level or a function level of the macrosteatotic hepatocytes. The level can be determined as disclosed herein.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

EXAMPLE

Experimental Procedures
Hepatocyte Isolation and Culture

Male lean Zucker rats, (Charles River, Wilmington, Mass.) (310±20 g) were housed in a 12 h light-dark cycle and temperature-controlled environment (25° C.) with water and standard chow ad libitum. All experimental procedures followed National Research Council guidelines and were approved by the Rutgers University Animal Care and Facilities Committee. Hepatocytes were isolated using a two-step in situ collagenase perfusion technique (Berthiaume et al., Journal of Surgical Research. 2009; 152(1):54-60 and Nagrath et al. Metabolic Engineering. 11(4-5):274-83). Viability was 90±4% as determined by trypan-blue exclusion (Nagrath et al. Metabolic Engineering. 11(4-5):274-83). Six-well culture plates (Beckton-Dickinson, Franklin Lakes, N.J.) were pretreated with 50 ug/ml rat type 1 collagen solution (Beckton-Dickinson) in 0.02M acetic acid (Sigma- Aldrich, St. Louis, Mo.) overnight at 4° C. and washed with phosphate buffered saline (PBS, Invitrogen, Grand Island, N.Y.). Freshly isolated hepatocytes were suspended ($10^6$ cells/ml) in standard hepatocyte medium and seeded ($10^6$ cells/well) as previously described (Nagrath et al. Metabolic Engineering. 11(4-5):274-83) (15). After incubating the cells at 37° C. in a 90% air/10% $CO_2$ atmosphere for 24 h, medium was removed and a collagen gelling solution (0.5 ml/well) was added to form a gel overlay (Nagrath et al. Metabolic Engineering. 11(4-5):274-83). Cultures were maintained in standard hepatocyte medium for 4 days with a fresh medium change every other day. Spent medium was collected (FIG. 1A, experimental days 1-5) for analysis.

Steatosis Induction and Reversal

Five-day hepatocyte cultures were switched to steatosis-inducing medium. Standard hepatocyte medium was supplemented with 2 mM oleic acid, 2 mM linoleic acid, and 4% (weight to volume) bovine serum albumin (Sigma-Aldrich) for 3 days, as previously described (Berthiaume et al., Journal of Surgical Research. 2009; 152(1):54-60 and Nagrath et al. Metabolic Engineering. 11(4-5):274-83). Medium was replaced with fresh steatosis-inducing medium for another 3 days of steatosis induction and the spent medium was collected (FIG. 1A, experimental days 5-11). These concentrations of free fatty acids (FFA) were chosen based on a dose response study to determine the FFA dose required to induce macrosteatosis, as indicated in FIG. 9. Following 6-day steatosis induction (11 days post-seeding), the medium was replaced with fresh hepatocyte medium with no steatosis reduction supplements (NSRS), or with a combination of the following steatosis reduction supplements (SRS): 10 uM forskolin, 1 uM GW7647, 10 uM scoparone (Sigma-Aldrich), 1 uM GW501516, 10 uM hypericin (Enzo, Farmingdale, N.Y.), 0.4 ng/ml visfatin (Biovision, Mountain view, Calif.) and amino acids (Invitrogen) at final concentrations described in FIG. 8. This cocktail promoted in vitro microsteatosis reduction by activating hepatocellular TG metabolism (Nagrath et al. Metabolic Engineering. 11(4-5):274-83). SRS medium pH was adjusted to match that of NSRS. Cells were incubated in SRS or NSRS medium for 48 h, after which (13 days post-seeding) the spent medium from all cultures was collected and replaced with NSRS medium for another 48 h. On post-seeding day 15, the spent medium from all experimental conditions was collected (FIG. 1A).

Hepatocyte Steatosis Assessment

A non-destructive quantitative image analysis method was used to quantify lipid droplet size distribution. Hepatocyte cultures were fixed in 4% paraformaldehyde, stained with the lipid-specific Nile red stain (Adipored™, Lonza, Walkersville, Md.), and counterstained with 1 ug/ml nuclei-specific Hoechst-33342 stain (Invitrogen), following the manufacturer recommendations. Confocal fluorescence images were obtained with an Olympus IX-80 microscope and analyzed using an in-house algorithm for edge detection, yielding unbiased measurements of size (cross sectional surface area) and lipid droplet distribution/cell. In addition, hepatocytes were scraped and sonicated in NSRS medium and using a lipase assay kit (Sigma-Aldrich), the TG content measured by quantification of liberated glycerol (Berthiaume et al., Journal of Surgical Research. 2009; 152(1):54-60). Time lapse bright-field images of hepatocytes undergoing macrosteatotic reduction were acquired every 15 minutes for 36 hours using a temperature and gas controlled (37° C. and 10% $CO_2$ balanced with air) Olympus IX-80 microscope stage. The size of individual lipid droplets was monitored using SLIDEBOOK™ software (Intelligent Imaging Innovations, Denver, Colo.) to calculate a rate of change in cross sectional surface area.

Hepatocyte Viability Assessment

Figure 5:
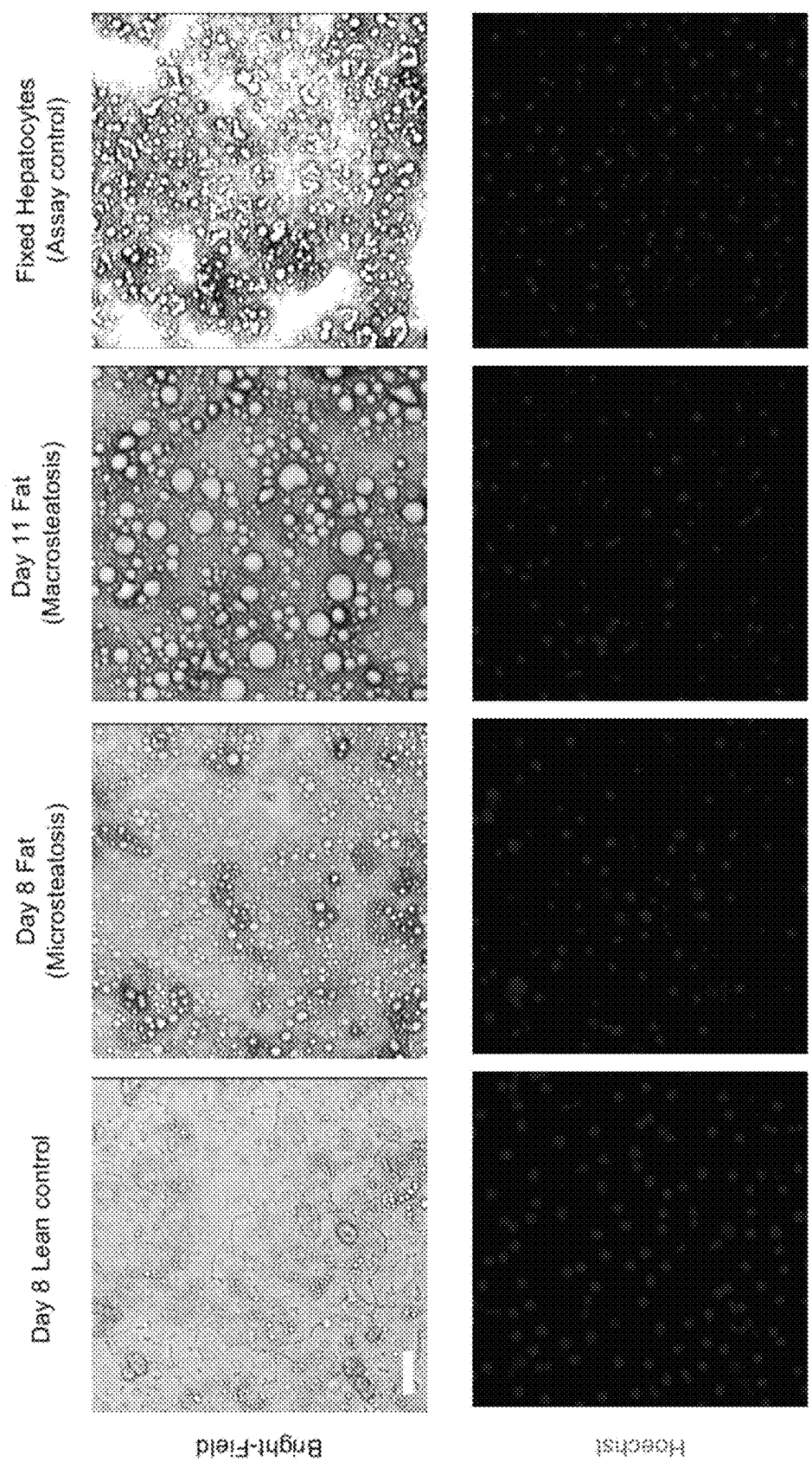
FIG. 5 is a set of photographs showing viability distribution in hepatocyte cultures after microsteatosis and macrosteatosis induction. Viable cell nuclei are stained with Hoechst (blue) but not EtHD-1 (red). Lean controls and methanol fixed cultures (which are all dead) are also shown for comparison. Bar=50 μm.

Cells were washed with PBS, and dead cells quantified following incubation with 4.29 ug/ml Ethidium Homodimer-1 (EthD-1, Invitrogen), and 1 ug/ml Hoechst-33342 (Invitrogen) to stain all cells, for 20 min at 37° C. (Maguire et al., Biotechnology and Bioengineering. 2006; 93(3):581-91). Five 20× epifluorescence images were obtained in 5 separate wells/experimental condition. Cells containing EthD-1 labeled nuclei were counted as dead, while those with Hoechst-stained nuclei were counted as live (FIG. 5). Percentage of viable cells was determined in each well and averaged for 5 wells/condition (Maguire et al., Biotechnology and Bioengineering. 2006; 93(3):581-91).

Hepatocyte Function Assessment

Rat albumin was measured by enzyme-linked immunosorbent assay (Bethyl laboratories, Montgomery, Tex.) and urea nitrogen using a biochemical assay (Stanbio), both using spent media samples and following the manufacturer's recommendations. Concentrations were normalized to the time period between medium changes and the number of viable hepatocytes to convert into specific secretion rates. Bile canaliculi function was assessed by visualization of excreted fluorescent products after incubation with 5-(and-6)-carboxy-2',7'-dichlorofluorescein diacetate (carboxy-DCFDA) (Sigma-Aldrich) at a final concentration of 2 uM. This molecule passively enters the cytoplasm of normal hepatocytes, where esterases metabolize it to a fluorescent product excreted into bile canaliculi (Tuschl et al., Chemico-Biological Interactions. 2009; 181(1):124-37). The nuclei were counterstained using Hochest-33342 as described above. Images were captured with an Olympus IX-80 microscope. General intracellular esterase activity was assessed using calcein-acetoxymethylester (calcein-AM, Invitrogen) at 5 μg/ml. Five epifluorescence images were captured using a 20× objective on an Olympus IX-80 microscope in 5 separate wells/experimental condition. The fluorescence levels obtained in each image were quantified using SLIDEBOOK™ software (Intelligent Imaging Innovations) and averaged for the 5 wells/condition.

Inducible cytochrome P450 activity was assessed as measured by breakdown of resorufin derivatives per established method (Tuschl et al., Chemico-Biological Interactions. 2009; 181(1):124-37) and found positive activity in all groups (data not shown). The insulin sensitivity was investigated via insulin withdrawal followed by induction as follows. The standard hepatocyte medium, which contains high levels of insulin (5 Units/ml, Sigma-Aldrich), was removed and the cultures were washed 3 times in PBS to remove any insulin residue. Insulin-free basal DMEM (Invitrogen) was added to the cells for 4 hours. Then, the medium was removed and either fresh insulin-free DMEM or insulin-rich DMEM (5 Units/ml, Sigma-Aldrich) was added to the cells for 30 minutes. Intrahepatocellular protein was extracted and analyzed for phosphorylated AKT (at Thr 308) as well as total AKT by Western blot using the appropriate antibodies (Cell Signaling Technology, Danvers, Mass.).

Human Liver Histology

Human liver tissue samples were obtained, stained with hematoxylin and eosin (H&E) and imaged as described in Guarrera et al., Journal of Surgical Research. 2011; 167(2): e365-e73.

Statistical Analysis

Results shown in text and graphs are mean±1 standard error. One-way ANOVA followed by Fisher's LSD post-hoc test was performed using KaleidaGraph (Synergy Software, Reading, Pa.). Values of p<0.05 indicate statistical significance.

Results

Macrosteatosis Induction in Primary Hepatocytes

Figure 1B:
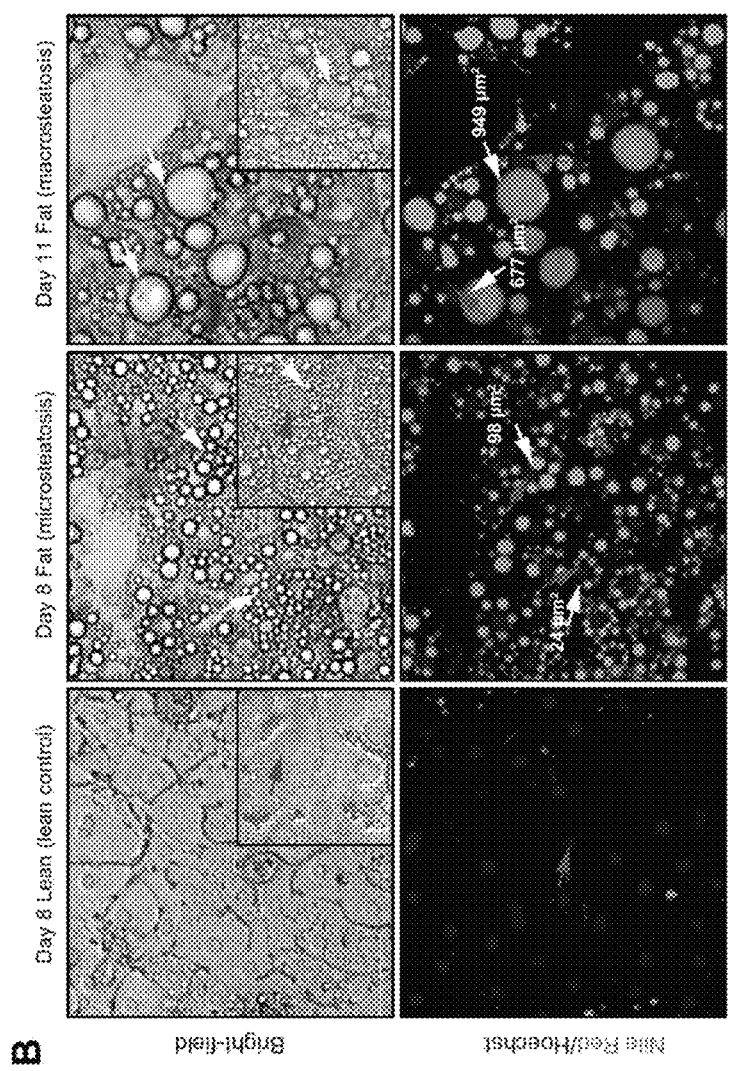

Incubation of collagen sandwiched hepatocytes with steatosis-inducing medium for 3 days (corresponding to 8 days post-seeding) induced a microsteatotic appearance and increased the TG content ~2.7 fold; consistent with prior studies (Berthiaume et al., Journal of Surgical Research. 2009; 152(1):54-60 and Nagrath et al. Metabolic Engineering. 11(4-5):274-83) (FIG. 1B-C). Incubation with steatosis-inducing medium for an additional 3 days increased the TG content even further, reaching ~5 fold the level in lean controls (FIG. 1B-C). This level is consistent with two in vivo models of liver macrosteatosis (ob/ob mouse and obese Zucker rat) where the intraheptic TG level is also ~5 fold the corresponding lean controls (Selzner et al., Journal of Hepatology. 2006; 44(4):694-701, and Washizu et al., Tissue Engineering. 2000; 6(5):497-504). The additional 3 days of steatosis induction also led to a dramatic increase in the lipid droplet size distribution (FIG. 1C). The number of lipid macrodroplets (cross-sectional surface area >350 um$^2$, defining a macrosteatotic lipid droplet (FIG. 6) increased 20-fold compared to the 3-day fatted cells (FIG. 1D). The 6-day fatted cells exhibited morphological characteristics found in macrosteatotic human livers, notably large intracellular lipid droplets displacing the nucleus to the cell periphery, as shown in FIGS. 1B and E. In addition, lipid droplet cross sectional surface area was comparable to that in macrosteatotic human livers (FIG. 1B, E). Hepatocyte viability was 85-90% after the 3-day and 6-day fattening protocols and was not significantly different from lean controls (Table 1A).

TABLE 1

Hepatocyte Viability. Percent viable hepatocytes of the experimental conditions at the relevant experimental days (based on images obtained from the EtHD-1 viability assay; sample viability staining is shown in FIG. 5). Data shown are means ± S.E. N = 5. No statistically significant change between treated hepatocytes and corresponding lean controls on the same experimental day.

| A | Day 8 | Day 11 |
|---|---|---|
| Lean Hepatocytes | 89.3% ± 1.0 | 88.5% ± 0.8 |
| Steatosis induced Hepatocytes | 85.4% ± 1.8 | 86.4% ± 2.0 |
| B | Day 13 | Day 15 |
| Lean Hepatocytes | 88.6% ± 1.2 | 85.6% ± 2.9 |
| Macrosteatosis | 82.0% ± 2.1 | 76.2% ± 2.5 |
| Macrosteatosis | 83.5% ± 1.9 | 74.0% ± 3.8 |

Reduction of Macrosteatosis in Primary Hepatocytes

Figure 2A:
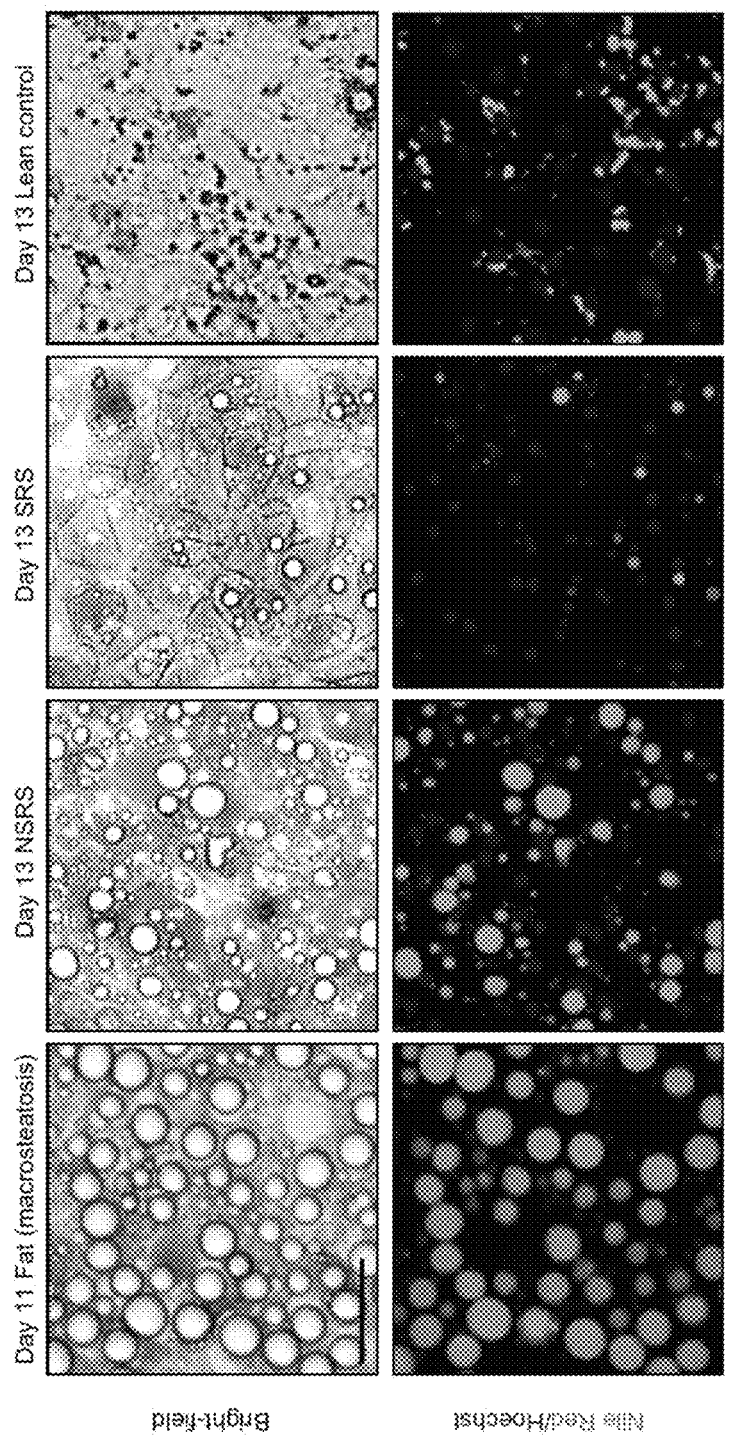
FIGS. 2A-D are a set of diagrams and photographs showing hepatocyte morphology and lipid content during macrosteatosis reduction. Macrosteatotic hepatocytes cultures were supplemented (SRS) or not (NSRS) with steatosis reducing agents for 2 days. A. Bright-field (top) and fluorescent images of Nile red and Hoechst stained macrosteatotic hepatocytes (bottom) after 2 days of culture. B, C. Macrosteatotic (>350 μm$^2$) droplet number and intracellular TG content for different steatosis reduction media. Means±S.E. N=6. •p<0.01 vs. D13 Lean. $^0$p<0.03 vs. D11 Fat. D. Bright-field images of initially SRS or NSRS treated macrosteatotic hepatocytes after 2 additional days of culture in NSRS medium compared to lean controls. Bar=50 μm.
Figures 2B, 2C:
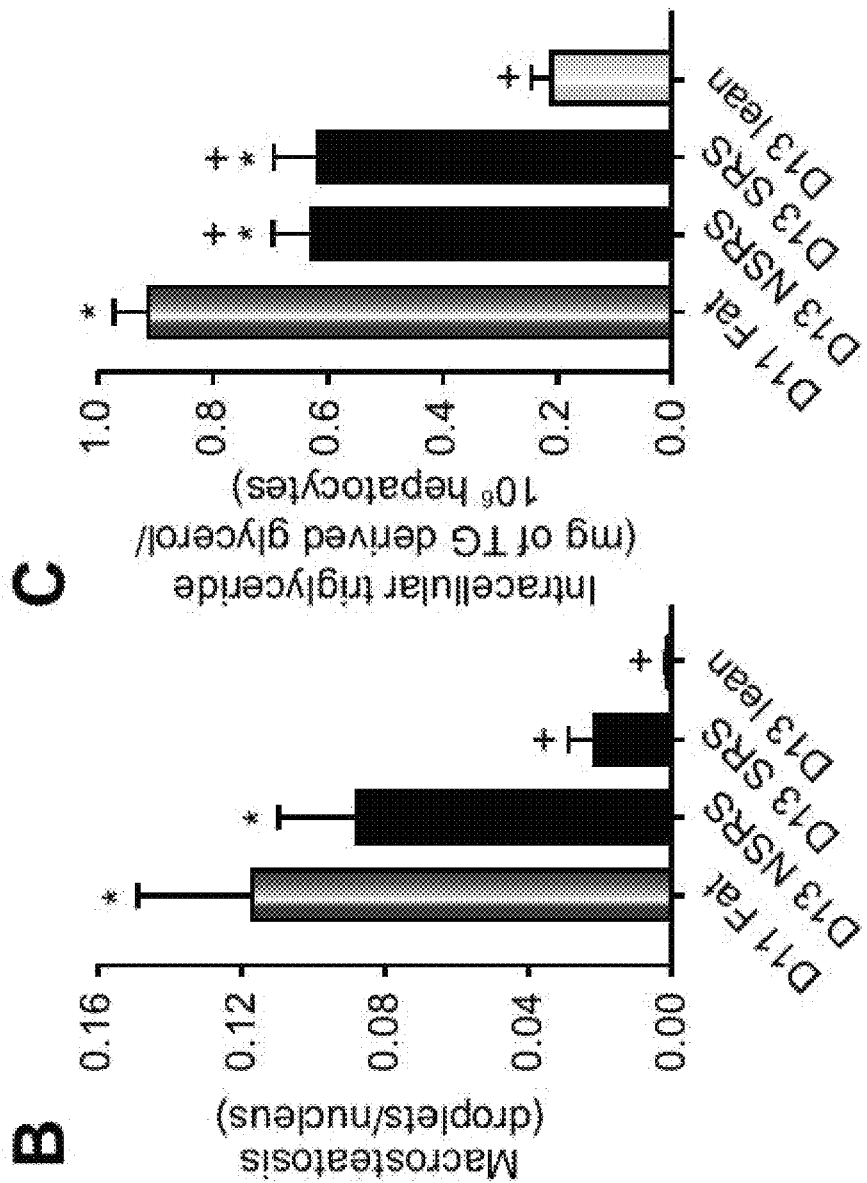

Using the 6-day macrosteatotic hepatocytes, the effect of macrosteatosis reduction on viability and liver-specific function was assessed. To accelerate macrosteatosis reduction, SRS previously shown to accelerate steatosis reduction in microsteatotic cultured hepatocytes, were utilized (Nagrath et al. Metabolic Engineering. 11(4-5):274-83). NSRS or SRS-containing medium was added to the macrosteatotic hepatocytes for 2 days. When SRS medium was used, macrosteatosis reduction was accelerated ~4-fold compared to NSRS medium to yield ~80% reduction within 2 days (FIG. 2A-B). Interestingly, both media compositions were equally effective in reducing TG content by ~30% during that time frame (FIG. 2C).

The size of individual lipid droplets in macrosteatotic hepatocyte cultures during the first 36 h macrosteatosis reduction period decreased linearly as a function of time, while the nucleus returned towards the center of the hepatocyte (FIGS. 7A-B).

Figure 2D:
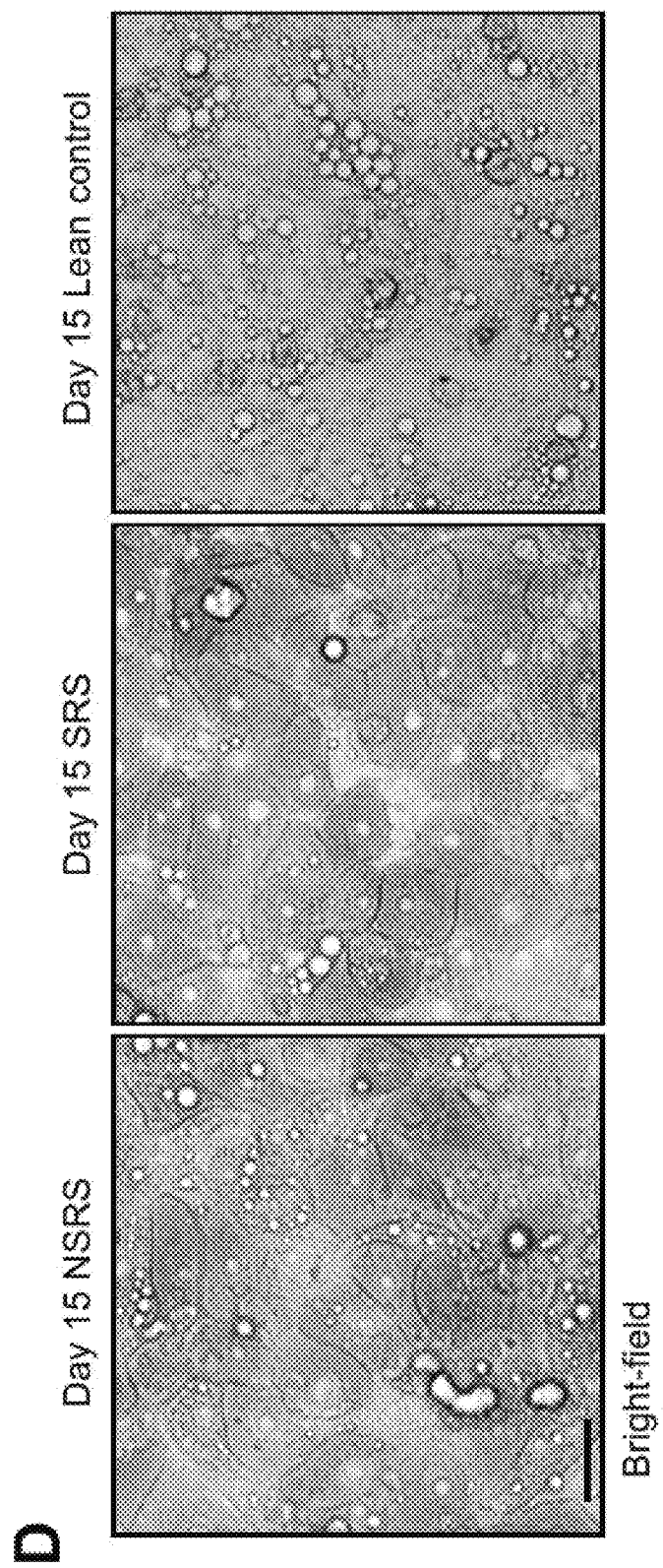

After 2 days in NSRS or SRS medium, all cells were switched to NSRS medium for an additional 2 days (days 13-15 post-seeding). At the end of this observation period, regardless of the medium used to reduce macrosteatosis for the first 2 days, the hepatocytes exhibited steatosis levels comparable to control lean hepatocyte cultures (FIG. 2D). Thus, while macrosteatotic hepatocytes can eventually exhibit lean-like lipid droplet distribution, SRS medium provides accelerated steatosis reduction during the first few hours.

Viability and Function Assessment

Figure 3A:
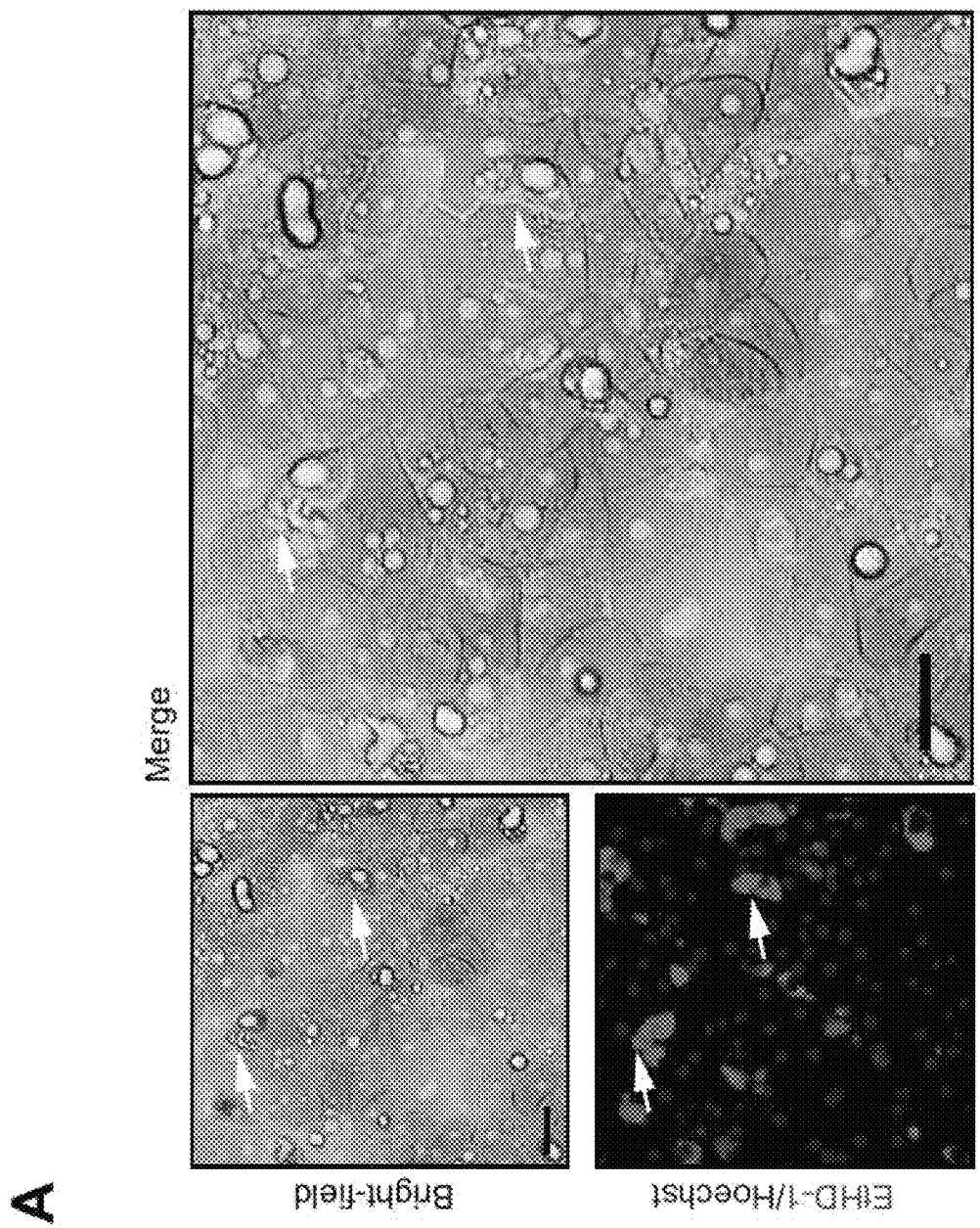
FIGS. 3A-C are a set of diagrams and photographs showing effect of steatosis induction and reversal on hepatocyte viability, albumin and urea secretion. Macrosteatotic hepatocytes were cultured in steatosis reducing medium until day 13 and then standard medium until day 15. A. Hepatocyte viability at the end of the steatosis reduction period (15 days post-seeding). Note that nonviable hepatocytes (EtHD-1$^+$) did not reduce steatosis. White arrows=EtHD-1$^+$ cells. Bar=50 μm. B, C. Albumin and urea secretion rates normalized to viable cell number. Means±S.E. N=6. *p<0.0001 vs. day 5 lean and $^+$p<0.01 vs. lean at the same time point.

As indicated in FIG. 3A, macrosteatosis reduction was uneven among the hepatocytes. Viability assessment revealed that reduction occurred only in the viable population (EtHD-1 negative), suggesting that active metabolism was critical. Nevertheless, during the first 2 macrosteatosis reduction days and the subsequent 2 days in NSRS medium, both SRS and NSRS medium treatments maintained hepatocyte viability similar to lean controls on the same experimental day (Table 1B).

Figures 3B, 3C:
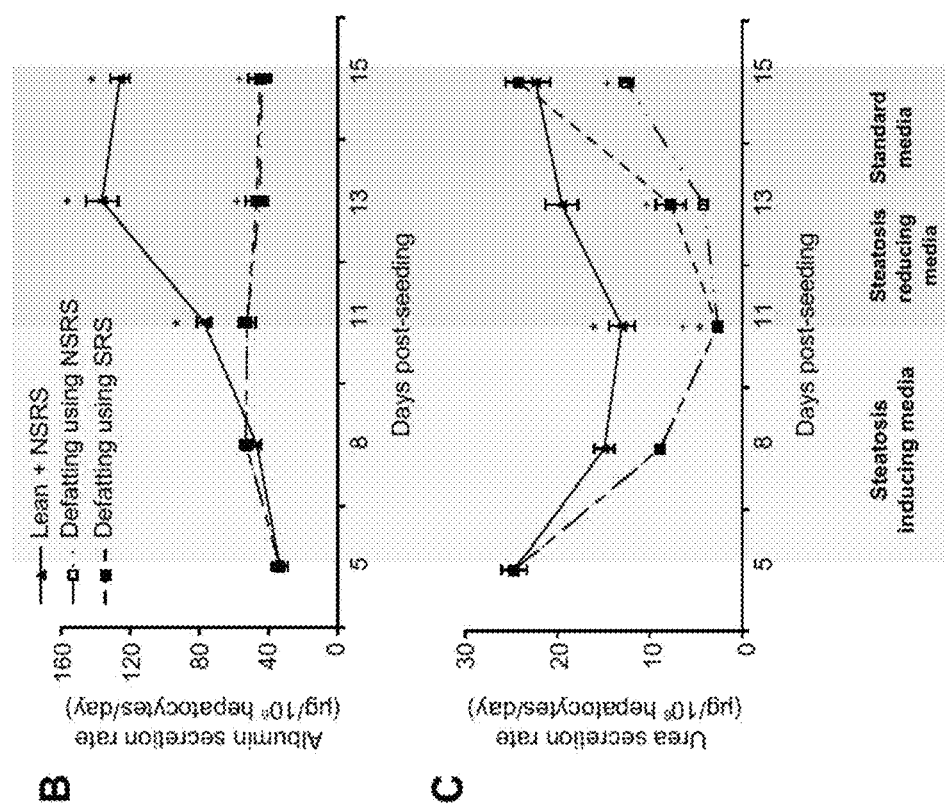

Next, cell function was assessed with liver-specific hepatocyte markers commonly used to assess the function of hepatocyte cultures and livers in transplantation settings including albumin and urea secretion rates (FIG. 3B-D), as well as bile canalicular morphology and function (FIG. 4) (Taneja et al., Transplantation. 1998; 65(2):167-72; Nakamuta et al., Transplantation. 2005 Sep. 15; 80(5):608-12; Guarrera et al., Journal of Surgical Research. 2011; 167(2): e365-e73; Jamieson et al., Transplantation. 2011; 92(3):289-95; Ninomiya et al., Transplantation. 2004; 77(3):373-9; Tuschl et al., Chemico-Biological Interactions. 2009; 181 (1):124-37; and Washizu et al., Tissue Engineering. 2000; 6(5):497-504). Microsteatotic hepatocytes maintained the albumin secretion rate and exhibited only a 1.7-fold decrease in urea secretion rates compared to lean hepatocyte cultures. On the other hand, macrosteatotic hepatocytes exhibited 1.5 fold lower albumin secretion levels and a 5-fold reduction in urea secretion levels compared to lean hepatocyte cultures (FIG. 3B-DC). Thus, macrosteatosis induction for 6 days had a more deleterious effect on hepatocyte function than microsteatosis induction for 3 days.

In macrosteatosis induction and reversal cycled hepatocytes, albumin secretion remained flat until the end of the observation time (day 15 post-seeding) below lean hepatocyte control levels and did not recover. In this respect, macrosteatotic reduced hepatocytes, treated with SRS or NSRS, behaved similarly (FIG. 3B). On the other hand, the urea secretion rate at the end of the observation period returned to ~50% of the lean hepatocyte culture levels in hepatocytes initially treated with NSRS and to ~100% in hepatocytes initially treated with SRS medium (FIG. 3C). During the last 2 days, all the cultures received NSRS medium. Therefore, the improved urea secretion recovery rate in hepatocytes initially treated with SRS medium at 15 days post-seeding can be attributed to the long-term effects of SRS treatment, such as the improved macrosteatosis reduction (FIG. 3C).

Figure 4A:
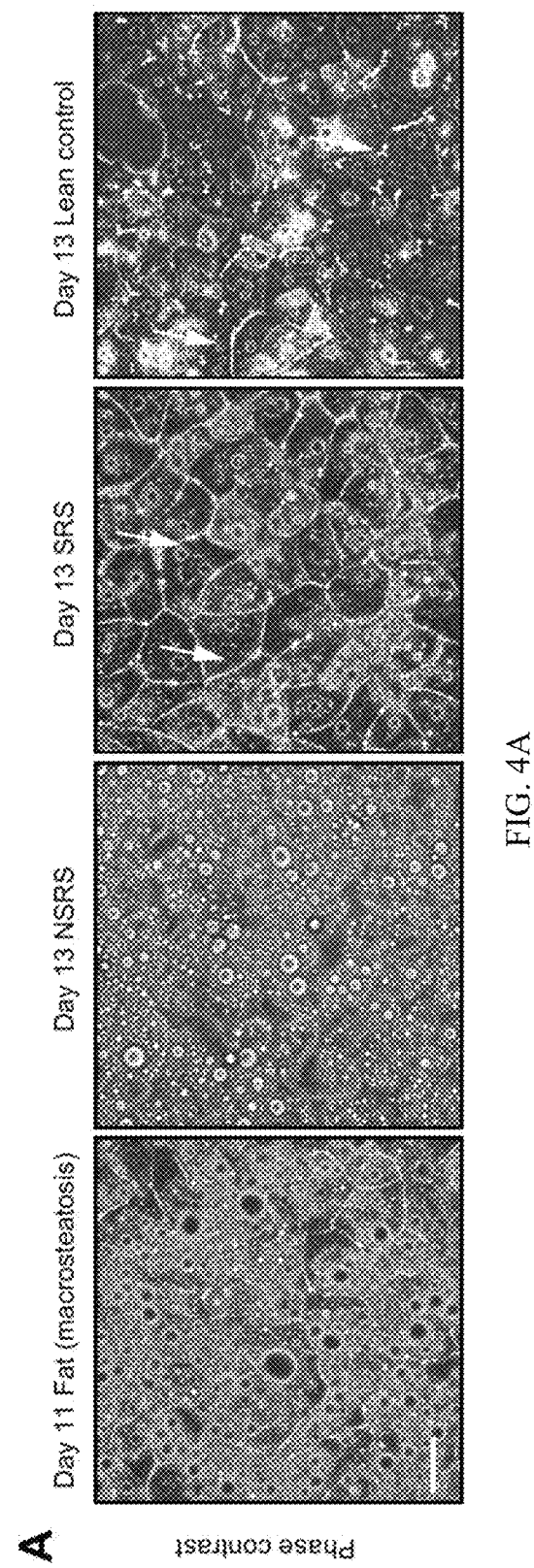
FIGS. 4A-D are a set of diagrams and photographs showing effect of steatosis induction and reversal on bile canaliculi morphology and function: A. Bile canalicular structures visualized by phase contrast appear as bright white hepatocyte borders (white arrows). B. Bright-field (top) and fluorescent images (bottom) of hepatocytes stained with green carboxy-DCFDA, which accumulates in functional bile canaliculi, and blue Hoechst, which stains nuclei. Bar=50 μm. C, D. Esterase activity, assessed by the accumulation of calcein in calcein-AM-incubated cells, is not significantly different between lean and macrosteatotic hepatocytes. Data shown are means±S.E. N=5.
Figure 4B:
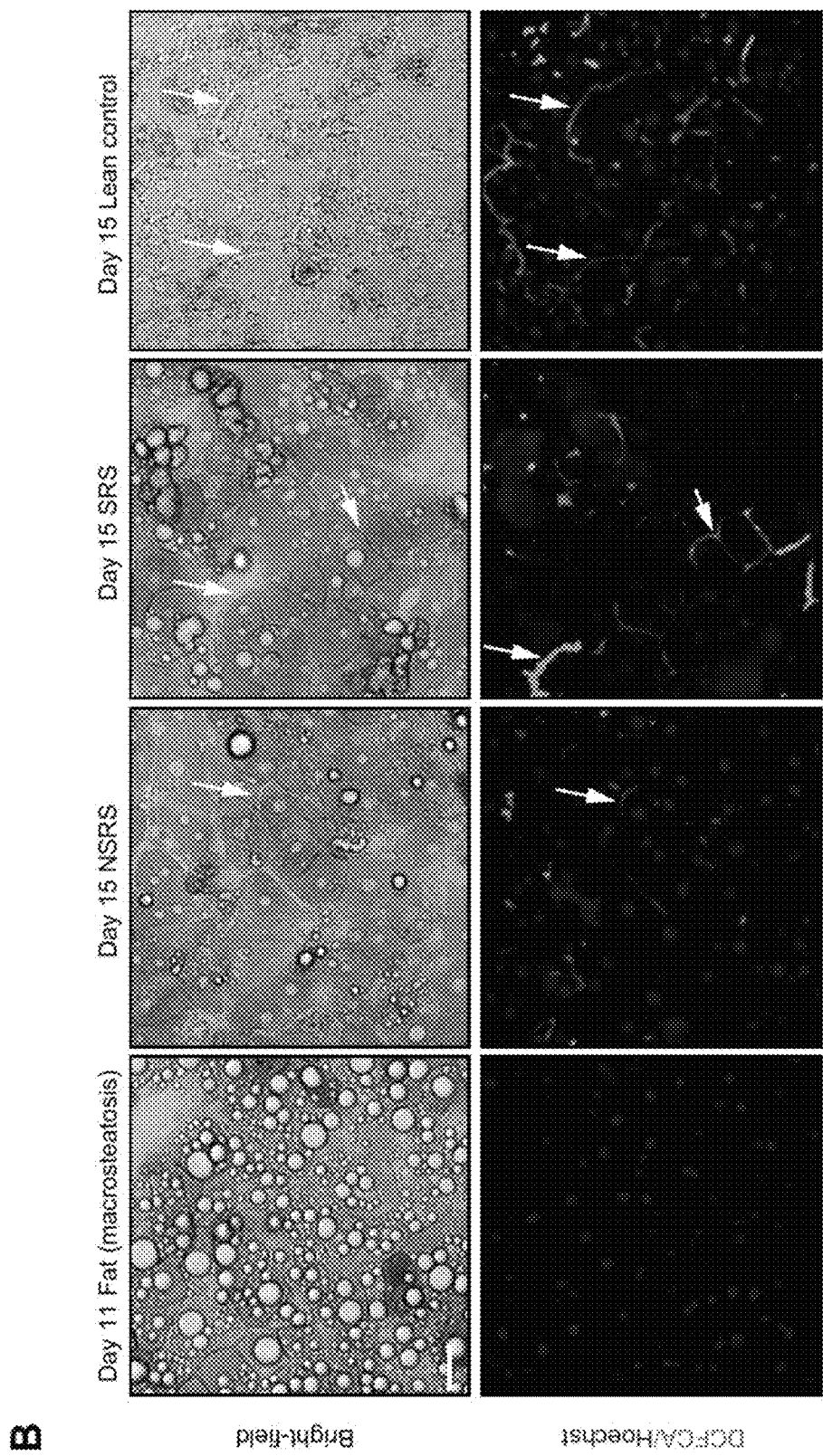
Figures 4C, 4D:
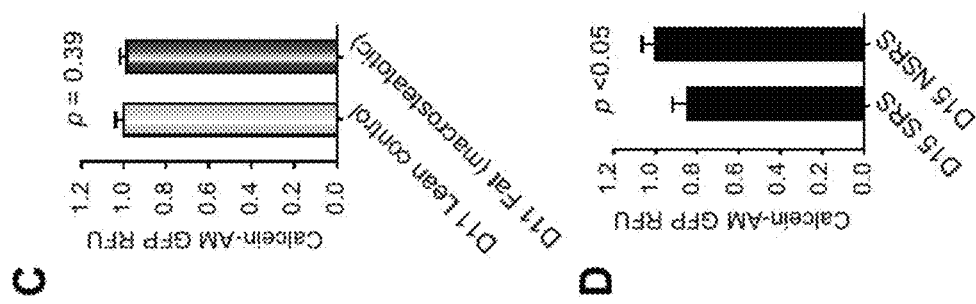

In lean hepatocyte cultures, bile canaliculi and the accumulation of fluorescent carboxy-DCFDA were easily visualized, suggesting a functional bile canalicular network (FIG. 4A-B), consistent with similar studies (Tuschl et al., Chemico-Biological Interactions. 2009; 181(1):124-37). In macrosteatotic hepatocytes, neither fluorescent carboxy-DCFDA nor the bile canalicular structure was observed (FIG. 4A-B). Because carboxy-DCFDA requires cleavage by intracellular esterases to fluoresce and eventually be transported into the bile, assays were carried out to investigate whether esterase activity was affected by macrosteatosis. Similar cultures were incubated with calcein-AM, which requires the same esterases to fluorescently label the cytoplasm. Calcein staining was similar in lean and macrosteatotic hepatocytes, suggesting no impairment in esterase activity (FIG. 4C). Thus, the lack of carboxy-DCFDA accumulation in macrosteatotic hepatocytes most likely reflects a disruption of the bile canalicular function.

Immediately following macrosteatosis reduction (13 days post-seeding), the bile canalicular morphology recovered completely to levels similar to lean controls, but only in hepatocytes treated with SRS medium (FIG. 4A). Bile canalicular function partially recovered after macrosteatosis reduction using NSRS medium, while it appeared nearly complete and comparable to lean controls after using the SRS medium (15 days post-seeding) (FIG. 4B). Similarly, the recovery in bile canalicular function was not attributed to levels of esterase activity (FIG. 4D).

In the assays, it was found that albumin secretion does not fully recover even if the culture time was extended. It is possible that the extent of defatting is not sufficiently complete to recover this particular function (since the data show that triglyceride content was still ~68% of macrosteatotic levels, thus remaining well above the "lean" baseline). In contrast, macrosteatosis had no effect on levels of hepatocyte nuclear factor 1-α, a transcription factor involved in the expression of many liver-specific genes, arguing against a de-differentiation of the cells due to excessive fat accumulation (Pontoglio et al. Cell 1996; 84:575-585).

The above data show that hepatocytes induced for macrosteatosis after 6 days exhibited lower albumin and urea secretion rates than those induced for microsteatosis after 3 days. This may be due to the direct effect of the increased lipid storage on these functions or to the difference in exposure times to FFA-rich medium. It is worth noting that in the clinic, albumin and urea blood data suggest that macrosteatotic patients are asymptomatic, although they exhibit elevated liver enzymes. These tests, however, do not equate the hepatocyte production rates, as in the above-described system, since blood levels are also affected by clearance mechanisms.

To explore the insulin sensitivity of the hepatocyte cultures, the response to insulin withdrawal followed by induction was investigated. A small increase in phosphorylated AKT could be seen after return to insulin-rich medium in both in lean and macrosteatotic cultures; however, the high baseline in phosphorylated AKT limited the ability to study insulin responsiveness in this model.

Figure 10:
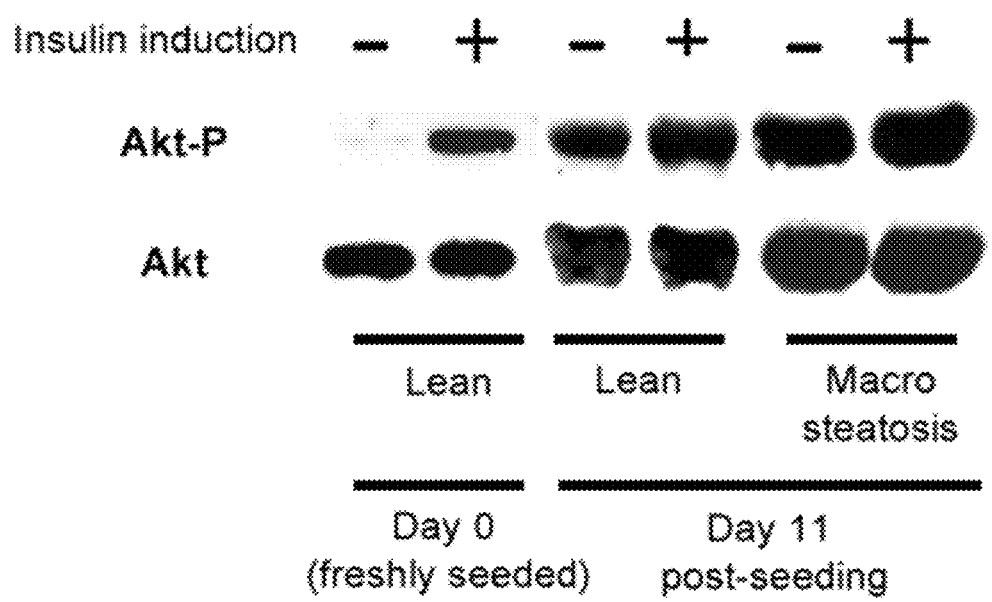
FIG. 10 is a photograph showing insulin induction-dependent AKT phosphorylation.

More specifically, Western blot analysis was carried out to examine AKT and phosphorylated AKT (at Thr 308). As shown in FIG. 10, each lane was loaded with intracellular protein extracted from 3 million hepatocytes. The blot was probed with antibodies for total AKT as well as for phosphorylated AKT. Data shown are representative of two separate experiments that yielded similar results. A small increase in phosphorylated AKT could be seen after return to insulin rich medium in both in lean and macrosteatotic cultures. It is noteworthy that hepatocytes that remained in insulin-free medium for 4 hours exhibited a relatively high baseline of phosphorylated AKT in both lean and macrosteatotic conditions, suggesting a fairly persistent activation of the insulin pathway. In contrast, freshly isolated and seeded hepatocytes that were never exposed to insulin rich media exhibited little phosphorylated AKT, while 30 minutes of insulin exposure significantly increased those levels, reaching an intensity comparable to the long-term cultures (both lean and macrosteatotic).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method of producing a population of cultured macrosteatotic hepatocytes, comprising:
providing a population of hepatocytes;
culturing said population of hepatocytes on a collagen matrix for a first period of time;
distributing a collagen gel solution over the hepatocytes to create a collagen sandwich configuration so that the hepatocytes are in the middle of the collagen sandwich configuration;
culturing the hepatocytes in the collagen sandwich configuration for a second period of time;
culturing the hepatocytes in a steatosis inducing medium for a third period of time to obtain said population of cultured macrosteatotic hepatocytes, wherein the third period of time is about 3-9 days.

2. The method of claim 1, wherein the first period of time is about 12 hours to 48 hours, about 18 hours to 30 hours, or about 24 hours.

3. The method of claim 1, wherein the second period of time is about 2 days to 3 weeks, about 5-7 days, or about 6 days.

4. The method of claim 1, wherein the third period of time is about 5-7 days, or about 6 days.

5. The method of claim 1, wherein the steatosis inducing medium contains one or more agent selected from the group consisting of a fatty acid, bovine serum albumin (BSA), insulin, glucose, and heparinized plasma.

6. The method of claim 5, wherein the fatty acid is oleic acid, linoleic acid, or palmatic acid.

7. The method of claim 1, wherein the population of hepatocytes is from a non-human mammal.

8. The method of claim 7, wherein the non-human mammal is a rodent.

9. The method of claim 1, wherein the population of hepatocytes is from a human.

10. The method of claim 1, wherein the macrosteatotic hepatocytes contain one or more large lipid droplets.

* * * * *

UNITED STATES PATENT AND TRADEMARK OFFICE
CERTIFICATE OF CORRECTION

PATENT NO. : 9,709,554 B2
APPLICATION NO. : 14/169605
DATED : July 18, 2017
INVENTOR(S) : Martin L. Yarmush et al.

Page 1 of 1

It is certified that error appears in the above-identified patent and that said Letters Patent is hereby corrected as shown below:

In the Specification

Delete the paragraph under GOVERNMENT INTERESTS on Column 1, Line number 12 and replace with the following:
--This invention was made with government support under grant numbers DK059766 and NS080733 awarded by the National Institutes of Health. The government has certain rights in the invention.--

Signed and Sealed this
Twenty-seventh Day of May, 2025

Coke Morgan Stewart
*Acting Director of the United States Patent and Trademark Office*